US010815456B2

(12) United States Patent
She et al.

(10) Patent No.: US 10,815,456 B2
(45) Date of Patent: Oct. 27, 2020

(54) COMPOSITION, KIT AND METHOD FOR CRYOPRESERVING CELLS

(71) Applicant: Transwell Biotech Co., Ltd, Hsinchu (TW)

(72) Inventors: Bin-Ru She, Hsinchu (TW); Kun-Chi Chiang, Hsinchu (TW); Cheng-Yi Lin, Hsinchu (TW); Ting-Yu Huang, Hsinchu (TW)

(73) Assignee: TRANSWELL BIOTECH CO., LTD., Hsinchu (TW)

( * ) Notice: Subject to any disclaimer, the term of this patent is extended or adjusted under 35 U.S.C. 154(b) by 116 days.

(21) Appl. No.: 15/723,934

(22) Filed: Oct. 3, 2017

(65) Prior Publication Data

US 2018/0092348 A1 Apr. 5, 2018

Related U.S. Application Data

(60) Provisional application No. 62/405,447, filed on Oct. 7, 2016, provisional application No. 62/404,170, filed on Oct. 4, 2016.

(51) Int. Cl.
*C12N 5/00* (2006.01)
*C12N 5/074* (2010.01)
(Continued)

(52) U.S. Cl.
CPC ......... *C12N 5/0018* (2013.01); *A01N 1/0221* (2013.01); *C12N 5/0068* (2013.01);
(Continued)

(58) Field of Classification Search
CPC ...... A01N 1/0221; A01N 1/02; A01N 1/0226; A01N 1/0231; A01N 1/0278; A01N 1/0294; A01N 1/0205; A61K 2300/00; A61K 35/28; A61K 35/12; A61K 9/19; A61K 47/34; A61K 31/737; A61K 38/18; A61K 41/0028; A61K 47/544; A61K 49/223; A61K 9/1271; A61K 31/12; A61K 31/4706; A61K 31/519; A61K 33/42; A61K 35/17; A61K 31/436; A61K 45/06; A61K 35/50; A61K 35/51; A61K 35/74; A61K 38/1808; A61K 38/1825; A61K 38/1833; A61K 38/1841; A61K 38/185; A61K 38/1858; A61K 38/1866; A61K 38/1891; A61K 38/19; A61K 38/204; A61K 38/2053; A61K 38/27; A61K 9/1623; A61K 9/1652; A61K 9/4816; A61K 9/4825; A61K 9/4858; A61K 9/4866; A61K 9/4891; A61K 35/36; A61K 31/4725; A61K 9/06; A61K 9/08; A61K 31/4709; A61K 47/02; A61K 47/06; A61K 47/10; A61K 47/14; A61K 47/183; A61K 47/22; A61K 47/38; A61K 31/381; A61K 31/472; A61K 38/1709;
A61K 48/005; A61K 31/165; A61K 31/437; A61K 31/47; A61K 31/56; A61K 9/0014; A61K 9/0048; A61K 2039/505; A61K 2039/507; A61K 31/14; A61K 31/198; A61K 31/277; A61K 31/341; A61K 31/343; A61K 31/4025; A61K 31/496; A61K 31/502; A61K 31/517; A61K 31/66; A61K 39/39533; A61K 49/00; A61K 2039/625; A61K 47/6925; A61K 48/00; A61K 9/0009; A61K 9/1272; A61K 9/145; A61K 9/146; A61K 9/5115; A61K 9/5146; A61K 9/5192; A61K 37/4725; A23L 3/375; A23L 33/135; C12N 5/0602; C12N 2501/90; C12N 2506/1346; C12N 5/0655; C12N 5/0663; C12N 2500/34; C12N 5/0018; C12N 5/0607; C12N 1/04; C12N 2501/998; C12N 2533/54; C12N 5/0068; C12N 5/0606; C12N 5/0636; C12N 5/0656; C12N 5/0693; C12N 9/1205; C12N 9/90; C12N 2500/32; C12N 2500/44; C12N 2500/90; C12N 2500/95; C12N 2501/12; C12N 2501/21; C12N 2501/23; C12N 2501/51; C12N 2501/515; C12N 2501/599; C12N 2501/70; C12N 2502/02; C12N 2506/02; C12N 2506/03; C12N 2509/00; C12N 2509/10;
(Continued)

(56) References Cited

U.S. PATENT DOCUMENTS 5,827,741 A 10/1998 Beattie et al.
6,723,497 B2 4/2004 Wolkers et al.
(Continued)

FOREIGN PATENT DOCUMENTS

CN 101220346 A 7/2008
CN 102771472 A 11/2012
(Continued)

OTHER PUBLICATIONS

International Search Report and Written Opinion in corresponding PCT Application No. PCT/CN2017/105253, dated Jan. 17, 2018.
(Continued)

*Primary Examiner* — Deborah K Ware
(74) *Attorney, Agent, or Firm* — Leason Ellis LLP (57) ABSTRACT

The present disclosure provides for a cryopreservation composition comprising a permeating cryoprotectant, a saccharide and a macromolecule. The cryopreservation composition has a low toxicity to cells and tissues, and promotes survival and retention of viability of the biological material during cryopreservation.

27 Claims, 1 Drawing Sheet

(51) Int. Cl.
*C12N 5/077* (2010.01)
*C12N 5/09* (2010.01)
*A01N 1/02* (2006.01)

(52) U.S. Cl.
CPC ......... *C12N 5/0607* (2013.01); *C12N 5/0656* (2013.01); *C12N 5/0693* (2013.01); *C12N 2533/54* (2013.01)

(58) Field of Classification Search
CPC ............ C12N 2510/00; C12N 2533/50; C12N 5/0605; C12N 5/061; C12N 5/0629; C12N 2533/52; C12N 15/8509; C12N 2799/022; C12N 2800/30; C12N 15/86; C12N 2740/10043; C12N 2740/13043; C12N 5/0634; Y10T 428/2984; C07K 14/43586; C07K 14/7051; C07K 14/70521; C07K 14/70539; C07K 14/70578; C07K 14/71; C07K 16/2863; C07K 2317/622; C07K 2319/00; C07K 2319/03; C07K 2319/41; C07K 2319/43; C07K 2319/70; C07K 14/395; C07K 14/475; C07K 16/2821; C07K 2317/92; C07K 14/315; C07K 16/2809; C07K 16/2818; C07K 2317/55; C12Y 502/00; A61D 19/02; A61L 2300/112; A61L 2300/412; A61L 2300/606; A61L 2300/64; A61L 2400/18; A61L 2420/02; A61L 2420/06; A61L 2430/02; A61L 2430/40; A61L 27/12; A61L 27/28; A61L 27/32; A61L 27/3834; A61L 27/3847; A61L 27/3895; A61L 27/425; A61L 27/54; A61L 27/58; A23V 2002/00; B03C 1/01; B03C 1/288; B03C 2201/18; B03C 2201/26; C07C 225/22; C07C 229/40; C07C 49/248; C07C 49/255; C07C 317/48; C07D 215/44; C07D 487/04; C07D 405/06; C07D 405/10; C07D 217/02; C07D 217/04; C07D 217/26; C12Q 1/6883; C12Q 2600/136; C12Q 2600/158; G01N 2015/1006; G01N 15/10; G01N 2015/1081; G01N 2333/916; G01N 33/502; G01N 33/5044; G01N 33/54333; G01N 33/5434; G01N 33/56966; G01N 33/5008; G01N 33/5088; G01N 2333/70503; G01N 2333/70525; G01N 2800/042; G01N 2800/164; G01N 33/6893; A61F 9/0017; F25D 25/00; F25D 31/005; A61P 29/00; A61P 27/02; A61P 11/02; A61P 11/06; A61P 17/00; A61P 17/02; A61P 17/06; A61P 17/08; A61P 17/14; A61P 27/14; A61P 43/00; A61P 1/00; A61P 3/10; A61P 9/10; A61P 1/02; A61P 1/04; A61P 37/00; A61P 37/02; A01K 2217/072; A01K 2227/105; A01K 2267/01; A01K 67/0275; B82Y 5/00

See application file for complete search history.

(56) References Cited

U.S. PATENT DOCUMENTS

| | | | |
|---|---|---|---|
| 8,420,307 B2* | 4/2013 | Ostermeier | A01N 1/02 435/2 |
| 8,512,941 B2 | 8/2013 | Natan | |
| 9,538,745 B2 | 1/2017 | He et al. | |
| 9,977,012 B2* | 5/2018 | Brockbank | A01N 1/0205 |
| 2006/0101539 A1 | 5/2006 | Ainley et al. | |
| 2008/0026361 A1* | 1/2008 | Ostermeier | A01N 1/02 435/2 |
| 2008/0176205 A1* | 7/2008 | Shelby | A01N 1/02 435/1.1 |
| 2009/0197331 A1 | 8/2009 | Kato et al. | |
| 2011/0250581 A1* | 10/2011 | Ostermeier | A01N 1/02 435/2 |
| 2013/0189669 A1* | 7/2013 | Ostermeier | A01N 1/02 435/2 |
| 2016/0116454 A1* | 4/2016 | Brockbank | A01N 1/0205 435/29 |
| 2017/0196221 A1 | 7/2017 | Zhu et al. | |
| 2017/0202212 A1 | 7/2017 | Gosiewska et al. | |
| 2018/0092348 A1* | 4/2018 | She | A01N 1/0221 |
| 2018/0094235 A1* | 4/2018 | Chang | C12N 5/0693 |

FOREIGN PATENT DOCUMENTS

| | | |
|---|---|---|
| CN | 105532643 A | 5/2016 |
| EP | 2885969 A1 | 6/2015 |
| WO | WO 2015/000972 A1 | 1/2015 |

OTHER PUBLICATIONS

Thompson et al., Cryopreservation and Thawing of Mammalian Cells, Dec. 2014, eLS, John Wiley & Sons, Ltd: Chichester. DOI: 0.1002/9780470015902.a0002561.pub2, pp. 1-7.
Gao et al., Mechanisms of Cryoinjury in Living Cells, ILAR Journal, 2000, 41(4): pp. 187-196.
Cohn et al., J. Am. Chem. Soc. 68 (1946) pp. 459-475.
Cryobiology, 41(4):pp. 257-279 (2000).
Choi et al., Applied Physics Letter 79: pp. 2252-2254, 2001.
Eastman et al., Applied Physics Letter 78: pp. 718-720, 2001.
International Preliminary Report on Patentability in corresponding PCT Application No. PCT/CN2017/105253, dated Apr. 9, 2019.
Extended European Search Report in EP 17857857, dated Mar. 19, 2020.

* cited by examiner

COMPOSITION, KIT AND METHOD FOR CRYOPRESERVING CELLS

CROSS REFERENCE TO RELATED APPLICATION

This application claims priority to U.S. Provisional Application Nos. 62/405,447 (filed on Oct. 7, 2016) and 62/404,170 (filed on Oct. 4, 2016), which are incorporated herein by reference in their entirety. This application is also related to International Application No. PCT/CN2017/105253, titled "Compositions and Methods for Maintaining Cell Viability" and filed on Oct. 4, 2017, which is incorporated herein by reference in its entirety.

TECHNICAL FIELD

The present disclosure relates generally to the field of cryopreservation. In particular, the present disclosure relates to compositions and methods for the cryopreservation of biological materials such as cells and tissues.

BACKGROUND OF THE DISCLOSURE

Cryopreservation techniques at temperatures at or below 0° C. are routinely used for long-time preservation of biological materials such as cells and tissues of animals (including human cells and tissues) and plants. Thompson et al., Cryopreservation and Thawing of Mammalian Cells, December 2014, eLS, John Wiley & Sons, Ltd: Chichester. DOI: 10.1002/9780470015902.a0002561.pub2. Effective long-term storage of mammalian cells is critical to the successful application of such cells as clinical and research tools. For example, stem cells can be used for cell transplantation, tissue engineering, and regenerative medicine. Cryopreserved oocytes, sperm, and embryos can be used in assisted reproductive technologies. In transplantation medicine, living tissues such as the skin, cornea, pancreatic islets and heart valves need to be cryopreserved.

It has been shown that the intracellular ice formation and osmotic imbalance could damage cells during the freezing process. Gao et al., Mechanisms of Cryoinjury in Living Cells, ILAR Journal, 2000, 41(4): 187-196. To avoid this, cryoprotectants (CPAs) are used to preserve the viability of the cells and tissues during freezing. Cryoprotectants are characterized into three main chemical classes: polyols (e.g., diols, glycerol), amides, and sulfoxides. Commonly used cryoprotectants include glycerol, dimethyl sulfoxide (DMSO), and polyethylene glycol (PEG). Furthermore, some additives, such as macromolecules and sugars, may be added to further decrease the damages on cells and tissues during cryopreservation.

Among these cryoprotectants, DMSO has a high cell permeability, and is the most effective and frequently adopted. However, DMSO is physiologically toxic and known to cause high blood pressure, nausea and vomiting when the cells are transfused to a recipient. Further, the toxicity of DMSO tends to debilitate the cells' survival rates and/or functions after the thawed cells are cultured or transfused into a recipient's body.

Slow freezing and vitrification are the two traditional approaches to the cryopreservation of biological materials. During slow freezing, the cells are cooled to temperatures slightly below their equilibrium freezing point and ice is seeded in the extracellular media. As ice forms in the extracellular solution, there is a progressive increase in the external solute concentration. As a result, the cell dehydrates, the melting point of the cytoplasm lowers and the formation of intracellular ice is avoided. Vitrification is defined by the viscosity of the sample reaching a sufficiently high value to behave like a solid but without crystallization. Principles of Cryopreservation, Methods in Molecular Biology, vol. 368: Cryopreservation and Freeze-Drying Protocols, Second Edition, Humana Press Inc. This glassy state can be induced in most liquids if cooling occurs rapidly. The addition of cryoprotectants can decrease the required high cooling rates.

The conventional techniques for the cryopreservation of mammalian cells are generally associated with disadvantages that detract from the potential use of the cells in clinical or research settings. Thus, there is a need for improved cryopreservation media and methods for cryopreserving biological materials.

SUMMARY

The present disclosure provides for a preservation composition (e.g., a cryopreservation composition) comprising: (1) about 2% (w/v) to about 40% (w/v) of a permeating cryoprotectant; (2) about 0.1 M to about 1 M of a saccharide; and (3) about 1% (w/v) to about 10% (w/v) of a macromolecule, where the unit of % (w/v) and the unit of M are based on the total volume of the preservation composition (e.g., the cryopreservation composition).

The present disclosure also provides for a preservation composition (e.g., a cryopreservation composition) comprising (or consisting essentially of, or consisting of): (1) about 2% (w/v) to about 40% (w/v) of a permeating cryoprotectant; (2) about 0.1 M to about 1 M of a saccharide; (3) about 1% (w/v) to about 10% (w/v) of a macromolecule; and (4) a solvent (e.g., water, a buffer, a saline solution, a culture medium such as Dulbecco's Modified Eagle Media (DMEM), or other solvent).

Also encompassed by the present disclosure is a preservation composition (e.g., a cryopreservation composition) comprising: (1) about 2% (w/v) to about 20% (w/v) of a permeating cryoprotectant; (2) about 0.1M to about 0.5 M of a saccharide; and (3) about 1% (w/v) to about 5% (w/v) of a macromolecule.

The present disclosure provides for a preservation composition (e.g., a cryopreservation composition) comprising (or consisting essentially of, or consisting of): (1) about 2% (w/v) to about 20% (w/v) of a permeating cryoprotectant; (2) about 0.1M to about 0.5 M of a saccharide; (3) about 1% (w/v) to about 5% (w/v) of a macromolecule; and (4) a solvent (e.g., water, a buffer, a saline solution, a culture medium such as Dulbecco's Modified Eagle Media (DMEM), or other solvent).

In certain embodiments, the preservation composition (e.g., the cryopreservation composition) is substantially free of DMSO.

In certain embodiments, the preservation composition (e.g., the cryopreservation composition) further comprises an amino acid, a cytokine, a lipid, a growth factor, an antibiotic, an antimycotic, a steroid hormone, a protein hormone, or a combination thereof.

In certain embodiments, the preservation composition (e.g., the cryopreservation composition) further comprises a biological material (e.g., one or more cells, a tissue(s), an organ(s), and/or viral particles). In certain embodiments, the cells are present in the preservation composition (e.g., the cryopreservation composition) at a concentration ranging from about $10^5$ cells/ml to about $10^7$ cells/ml.

In certain embodiments, the preservation composition (e.g., the cryopreservation composition) is in a cryopreserved state.

The present disclosure provides for a method for cryopreserving a biological material (e.g., one or more cells, a tissue(s), an organ(s), and/or viral particles), the method comprising the steps of: (a) contacting/mixing/combining the biological material (e.g., one or more cells, a tissue(s), an organ(s), and/or viral particles) with a cryopreservation composition (e.g., to form a mixture or to form a combination), and (b) freezing the mixture or the combination of the cryopreservation composition and the biological material (e.g., one or more cells, a tissue(s), an organ(s), and/or viral particles).

In certain embodiments, the mixture or the combination of the cryopreservation composition and the biological material (e.g., one or more cells, a tissue(s), an organ(s), and/or viral particles) is frozen at a temperature ranging from about −70° C. to about −200° C.

In certain embodiments, the cells are present in the mixture at a concentration ranging from about $10^5$ cells/ml to about $10^7$ cells/ml.

In certain embodiments, the method further comprises the step (c) thawing the frozen mixture or the combination of the cryopreservation composition and the biological material (e.g., one or more cells, a tissue(s), an organ(s), and/or viral particles).

In certain embodiments, the cells have a post-thaw viability of at least 70%, or at least 80%.

In certain embodiments, the permeating cryoprotectant comprises glycerol, polyethylene glycol, or a combination thereof.

In certain embodiments, the saccharide comprises sucrose, sorbitol, glucose, fructose, galactose, trehalose, mannose, maltose, or combinations thereof. In certain embodiments, the saccharide comprises sucrose, trehalose, or a combination thereof.

In certain embodiments, the macromolecule has a molecular weight ranging from about 65 kilodalton (kDa) to about 200 kDa. In certain embodiments, the macromolecule comprises albumin, gelatin, or a combination thereof.

In certain embodiments, the cells are mammalian cells. In certain embodiments, the cells are human, porcine, canine, equine or bovine cells. In certain embodiments, the cells comprise tumor cells. In certain embodiments, the cells comprise fibroblasts. In certain embodiments, the cells comprise stem cells.

The present disclosure provides for a kit comprising the present preservation composition (e.g., the cryopreservation composition).

DETAILED DESCRIPTION

The present disclosure provides for a preservation composition (e.g., a cryopreservation composition such as a freezing solution) comprising a permeating cryoprotectant, a saccharide (e.g., a sugar) and a macromolecule. The cryopreservation composition has a low toxicity to biological materials (e.g., cells, tissues or organs), and promotes survival and retention of viability of the biological material during the process of cryopreserving as well as in the cryopreserved state.

The biological material can then be used in a variety of research and clinical settings, for example, for cell-based therapeutics, in assisted reproductive technology, or for patients undergoing chemotherapy or radiation therapy. In one embodiment, due to the low toxicity of the present cryopreservation composition, the composition having the cells may be administered to a subject after thawing.

In certain embodiments, the present preservation composition is substantially free of dimethyl sulfoxide (DMSO), does not comprise DMSO, or is DMSO-free. In certain embodiments, the present composition demonstrates excellent cryoprotective effects comparable to that with the use of dimethyl sulfoxide (DMSO). In certain embodiments, the present composition demonstrates an equivalent or better cryoprotective effect as compared to that with the use of DMSO.

The present compositions and methods may be used for hypothermic preservation or for cryopreservation, including freezing and lyophilization.

The present disclosure provides for a preservation composition (e.g., a cryopreservation composition) comprising: (1) about 2% (w/v) to about 40% (w/v) of one or more permeating cryoprotectants; (2) about 0.1 M to about 1 M of one or more saccharides; and (3) about 1% (w/v) to about 10% (w/v) of a macromolecule (where the unit of % (w/v) and the unit of M are based on the total volume of the preservation composition.)

In certain embodiments, the present disclosure provides for a preservation composition (e.g., a cryopreservation composition) comprising (or consisting of, or consisting essentially of): (1) about 2% (w/v) to about 40% (w/v) of one or more permeating cryoprotectants; (2) about 0.1 M to about 1 M of one or more saccharides; (3) about 1% (w/v) to about 10% (w/v) of a macromolecule; and (4) a solvent. In certain embodiments, the solvent is water, a buffer, a saline solution, a culture medium such as Dulbecco's Modified Eagle Media (DMEM), or other solvent.

In certain embodiments, the present disclosure provides for a preservation composition (e.g., a cryopreservation composition) comprising: (1) about 2% (w/v) to about 20% (w/v) of one or more permeating cryoprotectants; (2) about 0.1 M to about 0.5 M of one or more saccharides; and (3) about 1% (w/v) to about 5% (w/v) of a macromolecule.

In certain embodiments, the present disclosure provides for a preservation composition (e.g., a cryopreservation composition) comprising (or consisting of, or consisting essentially of): (1) about 2% (w/v) to about 20% (w/v) of one or more permeating cryoprotectants; (2) about 0.1 M to about 0.5 M of one or more saccharides; (3) about 1% (w/v) to about 5% (w/v) of a macromolecule; and (4) a solvent. In certain embodiments, the solvent is water, a buffer, a saline solution, a culture medium such as Dulbecco's Modified Eagle Media (DMEM), or other solvent.

In certain embodiments, the permeating cryoprotectant comprises glycerol, polyethylene glycol, or a combination thereof.

In certain embodiments, the saccharide comprises sucrose, sorbitol, glucose, fructose, galactose, trehalose, mannose, maltose, or combinations thereof. In certain embodiments, the saccharide comprises sucrose, trehalose, or a combination thereof.

In certain embodiments, the macromolecule has a molecular weight (or an average molecular weight) ranging from about 30 kilodalton (kDa) to about 500 kDa, from about 40 kDa to about 400 kDa, from about 50 kDa to about 300 kDa, from about 60 kDa to about 300 kDa, from about 65 kDa to about 200 kDa, from about 65 kDa to about 150 kDa, from about 65 kDa to about 100 kDa, or from about 30 kDa to about 100 kDa.

In certain embodiments, the macromolecule comprises albumin, gelatin, or a combination thereof.

In certain embodiments, the present preservation composition comprises one, two, three, four, five, six or more permeating cryoprotectants at a concentration ranging from about 0.5% (w/v) to about 80% (w/v), from about 1% (w/v) to about 70% (w/v), from about 2% (w/v) to about 60% (w/v), from about 2% (w/v) to about 50% (w/v), from about 2% (w/v) to about 40% (w/v), from about 2% (w/v) to about 30% (w/v), from about 2% (w/v) to about 20% (w/v), from about 5% (w/v) to about 40% (w/v), from about 10% (w/v) to about 40% (w/v), from about 20% (w/v) to about 40% (w/v), from about 10% (w/v) to about 30% (w/v), from about 10% (w/v) to about 20% (w/v), from about 20% (w/v) to about 30% (w/v), or from about 5% (w/v) to about 50% (w/v) (of the total volume of the preservation composition).

In certain embodiments, the present preservation composition comprises one, two, three, four, five, six or more saccharides or sugars at a concentration ranging from about 0.05 M to about 2 M, from about 0.08 M to about 1.5 M, from about 0.1 M to about 1.2 M, from about 0.1 M to about 1.1 M, from about 0.1 M to about 1 M, from about 0.1 M to about 0.9 M, from about 0.1 M to about 0.8 M, from about 0.1 M to about 0.7 M, from about 0.1 M to about 0.6 M, from about 0.1 M to about 0.5 M, from about 0.1 M to about 0.4 M, from about 0.1 M to about 0.3 M, from about 0.2 M to about 1 M, from about 0.3 M to about 1 M, from about 0.4 M to about 1 M, from about 0.5 M to about 1 M, from about 0.6 M to about 1 M, from about 0.1 M to about 0.8 M, from about 0.1 M to about 0.6 M, from about 0.1 M to about 0.5 M, from about 0.1 M to about 0.4 M, or from about 0.1 M to about 0.3 M.

In certain embodiments, the present preservation composition comprises one, two, three, four, five, six or more macromolecules at a concentration ranging from about 0.5% (w/v) to about 20% (w/v), from about 0.6% (w/v) to about 18% (w/v), from about 0.8% (w/v) to about 16% (w/v), from about 1% (w/v) to about 15% (w/v), from about 1% (w/v) to about 12% (w/v), from about 1% (w/v) to about 10% (w/v), from about 1% (w/v) to about 9% (w/v), f from about 1% (w/v) to about 8% (w/v), from about 1% (w/v) to about 7% (w/v), from about 1% (w/v) to about 6% (w/v), from about 1% (w/v) to about 5% (w/v), from about 1.2% (w/v) to about 8% (w/v), from about 1.5% (w/v) to about 6% (w/v), from about 2% (w/v) to about 8% (w/v), from about 2% (w/v) to about 6% (w/v), from about 2% (w/v) to about 10% (w/v), or from about 5% (w/v) to about 10% (w/v) (of the total volume of the preservation composition).

As used herein, the percentage "% (w/v)" is percent weight to volume (w in gram and v in milliliter); the percentage "% (v/v)" is percent volume to volume; the percentage "% (w/w)" or "wt %" is percent weight to weight.

In certain embodiments, the composition comprises from about 300 mg/L to about 8,000 mg/L, from about 500 mg/L to about 7,000 mg/L, from about 1000 mg/L to about 6000 mg/L, from about 1000 mg/L to about 4500 mg/L, from about 500 mg/L to about 2300 mg/L, about 1,000 mg/L, about 4,500 mg/L, about 500 mg/L, or about 2,300 mg/L, of glucose.

In certain embodiments, the present preservation composition (e.g., cryopreservation composition) further comprises an amino acid, a cytokine, a lipid, a growth factor, an antibiotic, an antimycotic, a steroid hormone, a protein hormone, or a combination thereof.

In certain embodiments, the cryopreservation composition further comprises a biological material (one or more cells, a tissue(s), an organ(s), and/or viral particles). In certain embodiments, the cells are present in the cryopreservation composition at a concentration ranging from about $10^4$ cells/ml to about $10^8$ cells/ml, from about $10^5$ cells/ml to about $10^7$ cells/ml, from about $10^5$ cells/ml to about $10^8$ cells/ml, from about $10^4$ cells/ml to about $10^7$ cells/ml, about $10^5$ cells/ml, about $10^6$ cells/ml, or about $10^7$ cells/ml. The concentration of the cells in the preservation composition may be higher than $10^8$ cells/ml or lower than $10^4$ cells/ml. In certain embodiments, the concentration of the cells in the preservation composition can vary depending on the cell type. For example, for oocytes, the concentration of cells can be low, for example, as low as <1 cell/ml. The concentration can be determined by a skilled artisan for the particular cell type.

In certain embodiments, the present composition does not comprise a biological material (e.g., cells, tissues or organs).

The present disclosure provides for a method for cryopreserving a biological material (e.g., one or more cells, tissues, an organ(s), and/or viral particles). The method may comprise the steps of: (a) contacting/mixing/combining the biological material (e.g., one or more cells, tissues, an organ(s), and/or viral particles) with a cryopreservation composition (e.g., to form a mixture or to form a combination), and (b) freezing the mixture or the combination of the cryopreservation composition and the biological material (e.g., one or more cells, a tissue(s), an organ(s), and/or viral particles). In certain embodiments, the mixture or the combination of the cryopreservation composition and the biological material (e.g., one or more cells, a tissue(s), an organ(s), and/or viral particles) is frozen at a temperature ranging from about −70° C. and −200° C.

The present method may further comprise the step of (c) thawing the frozen mixture or the combination of the cryopreservation composition and the biological material (e.g., one or more cells, a tissue(s), an organ(s), and/or viral particles). In certain embodiments, the cells have a post-thaw viability of at least about 50%, at least about 60%, at least about 70%, at least about 75%, at least about 80%, at least about 85%, at least about 90%, or at least about 95%.

In certain embodiments, the cells comprise tumor cells. In certain embodiments, the cells comprise fibroblasts. In certain embodiments, the cells comprise stem cells.

In certain embodiments, the cells comprise mammalian cells, including, but not limited to, human, porcine, canine, equine or bovine cells.

The present method may further comprise the step of administering the thawed biological material to a subject (e.g., a patient). U.S. Patent Publication No. 20090130756.

The present disclosure provides for a method for preserving (e.g., cryopreserving) a biological material. The method may comprise the following steps: (a) combining/mixing/contacting the present preservation composition with a biological material; (b) cooling and/or freezing the mixture; and (c) storing the biological material (e.g., at appropriate storing conditions).

The biological material may be added to the preservation composition. Alternatively, the preservation composition can be added to the biological material. In certain embodiments, in step (a) of the method, the biological material (e.g., the cells) are suspended in the preservation composition.

The temperature(s) suitable for freezing or storing the biological material may vary. For instance, cells may be frozen or stored at a temperature ranging from about −70° C. to about −200° C. In one embodiment, cells may be frozen or stored at or above the boiling temperature of liquid nitrogen, i.e., at or above about −196° C.

In certain embodiments, the preservation composition is a hypothermic preservation composition (e.g., a hypothermic preservation solution). In certain embodiments, the preservation composition is a cryopreservation composition (e.g., a cryopreservation solution). In such case the solution may be for example a freezing solution (in which case the biological material is frozen) or a lyophilization solution (in which case the biological material is lyophilized).

In certain embodiments, the present cryopreservation composition (with or without a biological material) is in a cryopreserved state (or a frozen state), or has been thawed from a cryopreserved state. In certain embodiments, the present cryopreservation composition (with or without a biological material) is in a hypothermic state, or in a freeze-dried state.

The cryopreservation composition (which also comprises a biological material) in a cryopreserved state may be obtained by slow-freezing or vitrification. U.S. Pat. No. 9,458,424.

The present preservation composition may be a liquid or a solid. In certain embodiments, the present preservation composition is a concentrate composition, such as, in a dry form (e.g., powder, tablet, granular or any other suitable physical form) or in liquid form as, e.g., 2×, 3×, 4×, 5×, 6×, 7×, 8×, 9×, 10×, 15×, 20× etc. stock solutions. The stock solutions can be diluted 2×, 3×, 4×, 5×, 6×, 7×, 8×, 9×, 10×, 15×, 20× etc. by, e.g., a culture medium, a physiologic solution, a buffer, water etc. The dry form of the preservation composition may be converted to a liquid form by adding, e.g., a culture medium, a physiologic solution, a buffer, water etc. (e.g., dissolved in, e.g., a culture medium, a physiologic solution, a buffer, water etc.).

In certain embodiment, the concentrations of the components discussed herein are the concentrations of the components in a stock solution of the present preservation composition. In certain embodiment, the concentrations of the components discussed herein are the concentrations of the components in a working solution of the present preservation composition.

The present preservation composition may be a solution. In certain embodiments, the composition is an aqueous solution of the components discussed herein (e.g., one or more permeating cryoprotectants, one or more saccharides, and one or more macromolecules).

In certain embodiments, when preparing the present composition, the components discussed herein (e.g., one or more permeating cryoprotectants, one or more saccharides, and one or more macromolecules) are dissolved in a balanced electrolyte solution (e.g., a saline solution, a culture medium such as a cell culture medium). In certain embodiments, the preservation solution has an appropriate concentration of electrolytes (such as sodium, potassium, and/or chloride ions) to maintain a normal osmolality. Suitable saline solutions for use in cryopreservation are well known in the art. In one embodiment, the saline solution is a phosphate-buffered saline solution (PBS). In one embodiment, the saline solution comprises one or more of the following: Sodium Chloride, Potassium Chloride, Magnesium Sulfate, Potassium Phosphate, Calcium Chloride, and Sodium Bicarbonate.

The present preservation composition may comprise a buffer system (e.g., a physiological buffer). The present preservation composition may comprise a balanced salt solution or any physiological solution.

Non-limiting examples of the buffer systems include phosphoric acid buffers (for example, phosphate buffered saline (PBS)), BES, TES, acetamidoglycine, glycine amides, glycylglycine, TRICINE, TALP, tris-ethanolamine, veronal, and HEPES.

In certain embodiments, the concentration of the buffer in the present composition ranges from about 1 mM to about 1000 mM, from about 1 mM to about 200 mM, from about 5 mM to about 200 mM, or from about 5 mM to about 50 mM.

Non-limiting examples of culture media include, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, RPMI 1640 Media, and combinations thereof and/or modifications thereof.

In certain embodiments, the present composition has a pH ranging from about 6.0 to about 8.5, from about 6.5 to about 8, from about 6.9 to about 7.5, or from about 7.2 to about 7.4, at room temperature or ambient temperature (for example, at 25° C.).

In certain embodiments, the preservation composition is packaged in unit forms. In one embodiment, the cryopreservation composition is packaged in a volume of 10 ml, 50 ml, 100 ml, 500 ml or 1 L. In certain embodiments, the preservation composition is packaged as a 1×, 5×, 10×, or 20× solution.

The present composition can be obtained in a solid form by mixing the components discussed herein, or as an aqueous solution by dissolving the components in water, a buffer, a solution, a culture medium, etc.

Definitions

The term "preservation" refers to the process of maintaining a biological material under conditions in which its biological activity is considerably reduced while it nonetheless remains viable and may resume essentially normal biological activity when taken out of the preservation state. Specific examples of preservation are cryopreservation and hypothermic preservation.

The term "preservation composition" relates to a composition (or a composition when diluted or dissolved) permitting the preservation of a biological material, such that the biological material retains its viability. A specific embodiment of a preservation composition is one for preserving biological material at low temperatures. In certain embodiments, the preservation composition is a preservation solution. Hypothermic preservation compositions and cryopreservation compositions are examples of preservation compositions.

The term "cryopreservation" refers to a process including at least one step of lowering the temperature of a biological material from a temperature that is above the freezing temperature of the biological material (or of a mixture of the biological material and a preservation composition) to a temperature that is below that freezing temperature. Cryopreservation encompasses freezing, vitrification and lyophilization. The term "cryopreservation of cells" means to freeze and preserve cells for the purpose of maintaining the cells over a desired period of time without sub-culturing.

The terms "cryopreservation composition", "cryopreservation medium", or "freezing composition", refer to a composition or medium (or a composition when diluted or dissolved) in which a biological material is immersed before cryopreservation or freezing, or to a composition or medium which can be used to treat the cells or tissues prior to freezing. A cryopreservation composition contains one or more cryoprotectants. In certain embodiments, a cryopreservation solution may be a freezing solution, a vitrification solution, a lyophilization solution and/or a mixture of such solutions. In certain embodiments, a cryopreservation composition is a cryopreservation solution. In certain embodiments, the cryopreservation composition refers to a composition or medium for storing or freezing a biological material at a temperature at or below about 8° C., at or below about 4° C., at or below about 0° C., at or below about −20° C., at or below about −70° C., at or below about −135° C., at or below about −196° C., or in liquid nitrogen.

The term "appropriate freezing conditions" or "appropriate cryopreservation conditions" means such freezing conditions that would maintain a biological material in a viable state.

The term "hypothermic preservation" means preservation at a temperature below the physiological temperature but above freezing, wherein biological processes are slowed down thus allowing prolonged storage of biological material (e.g., below 8° C. and above 0° C., or between 4° C. and 8° C.).

The term "hypothermic preservation composition" means a preservation composition comprising such components that would allow the biological material to withstand a temperature below 8° C. and the necessary metabolites to sustain its viability at such temperature.

The term "vitrification" refers to a process of converting a material into a glass-like amorphous solid which is free of any crystalline structure. Vitreous solidification occurs at the glass transition temperature.

The term "non-linear cooling" refers to a process of cryopreservation for which, by design, temperature versus time is other than a single straight line or a profile made of two line segments with different slopes. In one embodiment, a non-linear cooling cryopreservation method is achieved by a non-constant cooling rate during at least a portion of the method. In another embodiment, the non-linear cryopreservation method is achieved by a two-step cooling process, wherein the cells or tissue are cooled at a constant or non-constant rate to a first temperature and then subsequently at a constant or non-constant rate to a second temperature (e.g., storage temperature).

"Storage Temperature" is the temperature at which the biological material is stored. In certain embodiments, the storage temperature is at or below about 8° C., at or below about 4° C., at or below about 0° C., at or below about −20° C., at or below about −60° C., at or below about −70° C., at or below about −135° C., at or below about −196° C., or in liquid nitrogen.

The term "substantially free" of an agent should be understood as meaning free of the agent, or that any amount of the agent present in the preservation composition is so low so as not to have any effect on the preservation process, on the outcome of the preservation process or on the properties of the biological material (for example the viability of living matter, e.g., cells, if such are included in such material) after it is taken out of the preservation conditions. In certain embodiment, the term "substantially free" of an agent means that the agent is less than about 5 w/w (or % w/v, or % v/v), less than about 4% w/w (or % w/v, or % v/v), less than about 3% w/w (or % w/v, or % v/v), less than about 2% w/w (or % w/v, or % v/v), less than about 1% w/w (or % w/v, or % v/v), less than about 0.5% w/w (or % w/v, or % v/v), less than about 0.2% w/w (or % w/v, or % v/v), less than about 0.1% w/w (or % w/v, or % v/v), less than about 0.05% w/w (or % w/v, or % v/v), less than about 0.02% w/w (or % w/v, or % v/v), or less than about 0.01% w/w (or % w/v, or % v/v).

The term "about" in reference to a numeric value refers to +10% of the stated numeric value. In other words, the numeric value can be in a range of 90% of the stated value to 110% of the stated value.

Cryoprotectants

The term "cryoprotectant" or "cryoprotective agent" herein refers to a compound used to slow or prevent ice nucleation, ice-crystal growth, ice formation, or any combination thereof. Cryoprotectants help maintain the viability of the biological material under cryopreservation and prevent the biological material from damage that may be caused in cryopreservation.

Cryoprotectants include permeating cryoprotectants and non-permeating cryoprotectants.

Permeating cryoprotectants are cryoprotectants that can penetrate the cell membrane and be present intracellularly. Non-limiting examples of permeating cryoprotectants include glycerol, polyethylene glycol, ethylene glycol, propylene glycol (1,2-propanediol, propane-1,2-diol), and DMSO.

Non-permeating cryoprotectants are cryoprotectants that do not penetrate the cell membrane and remain in the extracellular solution. Non-limiting examples of non-permeating cryoprotectants include high molecular weight molecules, such as saccharides (e.g., sucrose, trehalose, maltose), sugars, starches (e.g., hydroxyethyl starch), protein (e.g., albumin such as serum albumin), percoll, ficol, polyethylene glycol, dextran, polyvinyl pyrrolidone, polyvinyl-alcohol (PVA), serum, plasma and other macromolecules. In certain embodiments, the present composition comprises a non-penetrating cryoprotectant which has a molecular weight greater than or equal to about 342 daltons (which is the molecular weight of sucrose).

Non-limiting examples of cryoprotectants also include, methoxylated compounds, ethanol, 2-methoxy ethanol, 1,2-dimethoxyethane, 1-methoxy]-2-propanol, and glycerol derivatives, such as 3-methoxy-1,2-propanediol or 1,3-dimethoxy-2-propanol. In certain embodiments, the present composition comprises, or is free of, one or more methoxylated compounds as a cryoprotectant. In certain embodiments, the present composition comprises, or is substantially free of, one or more diols as a cryoprotectant.

The present composition may comprise one or more permeating cryoprotectants, one or more non-permeating cryoprotectants, or a combination of one or more permeating cryoprotectants and one or more non-permeating cryoprotectants.

Saccharides

Saccharides include oligosaccharides such as monosaccharides and disaccharides, polysaccharides, and the like. Saccharides include sugars.

Non-limiting examples of saccharides include sucrose, sorbitol, glucose, fructose, galactose, trehalose, mannose, raffinose, stachyose, dextran, xylose, arabinose, mannitol, xylitol, myo-inositol, lactose, maltose, cellobiose, lactitol, maltitol, methyl cellulose, carboxymethyl cellulose, glycogen, amylose, amylopectin, inulin, sodium alginate, ethyl cellulose, hydroxyethyl cellulose, xanthan gum, glucosamine, galactosamine, and combinations thereof. U.S. Pat. Nos. 6,673,607 and 7,094,601.

Albumin

Non-limiting examples of albumin include serum albumin (e.g., human serum albumin or HSA), plasma albumin (e.g., human plasma albumin), bovine serum albumin, and/or synthetic serum albumin), ovalbumin, plant albumin, or combinations thereof. Non-limiting examples of albumin also include fetal bovine serum.

Albumin may be either of natural origin (e.g., purified from a natural source) or of recombinant origin (recombinant albumin) In one embodiment, albumin is produced by purification from biological material of human origin. It may be obtained by conventional techniques for fractionation of plasma obtained from blood (Cohn et al., J. Am. Chem. Soc. 68 (1946) 459 pp), or by extraction from the human placenta, according to the technique described by J. Liautaud et al. (13th International IABS Conference, Budapest; A: "Purification of proteins. Development of biological standard", Karger (ed.), Bale, 27 (1973) 107 pp). In one embodiment, recombinant albumin is produced in a eukaryotic host.

In one embodiment, the term "albumin" comprises any natural variant of human albumin, resulting from the polymorphism of this protein.

Gelatin

In certain embodiments, gelatin in the present preservation composition has a molecular weight (or weight average molecular mass, or average molecular mass) ranging from about 15 kilodalton (kD) to about 40 kD, from about 25 kD to about 40 kD, from about 25 kD to about 50 kD, from about 25 kD to about 45 kD, from about 40 kD to about 50 kD, from about 10 kD to about 100 kD, from about 40 kD to about 100 kD, from about 50 kD to about 100 kD, from about 100 kD to about 200 kD, from about 100 kD to about 250 kD, from about 80 kD to about 200 kD, from about 150 kD to about 200 kD, from about 100 kD to about 150 kD, or from about 50 kD to about 200 kD.

In certain embodiments, gelatin has an isoelectric point (pI) ranging from about 4.5 to about 9, from about 5 to about 9, from about 5 to about 7, from about 6 to about 7, from about 5 to about 6, from about 7 to about 9, or from about 4.7 to about 5.2.

In certain embodiments, gelatin is derived from mammalian tissue. In certain embodiments, gelatin is obtained from animal collagen. In certain embodiments, gelatin is derived from raw materials including, but not limited to, the skin, bones, connective tissues, tendons, ligaments, etc. of animals such as cattle, chicken, pigs, and fish. In one embodiment, gelatin is of bovine source, porcine source, or a combination thereof. In certain embodiments, gelatin is sourced from bovine bones, porcine skin, bovine skin, pork, bovine hides, and/or fish skin. In one embodiment, gelatin is skin-derived gelatin, and/or bone-derived gelatin.

In certain embodiments, gelatin is a mixture of peptides and proteins produced by partial hydrolysis of collagen. In certain embodiments, gelatin is a hydrolyzed form of collagen. In certain embodiments, gelatin is a form of denatured collagen.

In certain embodiments, gelatin may be type A gelatin or type B gelatin. As used herein, type A gelatin is the gelatin obtained from acid-treated raw material; type B gelatin is the gelatin obtained from alkali-treated raw material.

In certain embodiments, to produce gelatin, collagen hydrolysis is performed by chemical hydrolysis, and/or thermal hydrolysis. In one embodiment, collagen is boiled (e.g., in water) or heated (extensively) to produce gelatin.

In certain embodiments, to produce gelatin, collagen hydrolysis is performed by acid-hydrolysis, alkali-hydrolysis, and/or enzymatic hydrolysis.

In certain embodiments, the manufacturing processes of gelatin contain three main stages: the pretreatment, the main extraction step, and the refining and recovering treatments. Pretreatments make the raw materials ready for the main extraction step and remove impurities that may have negative effects on physiochemical properties of the final gelatin product. The main extraction step may be done with hot water or dilute acid solutions as a multistage extraction to hydrolyze collagen into gelatin. The refining and recovering treatments include filtration, clarification, evaporation, sterilization, drying, rutting, grinding, and/or sifting to remove the water from the gelatin solution, to blend the gelatin extracted, and/or to obtain dried, blended and ground final product.

Other Components

In certain embodiments, the present composition may further comprise amino acids, cytokines, lipids, growth factors, antibiotics (e.g., penicillin, streptomycin, etc.), antimycotics, steroid hormones, protein hormones, serum, proteins, salts, formamide, methoxylated compounds, and/or polymers (e.g., polyvinyl pyrrolidone and polyvinyl alcohol).

Amino Acids

The present preservation composition may or may not comprise one or more amino acids.

Amino acids include optical isomers, namely both D-isomers and L-isomers. Amino acids include alpha-amino acids, as well as beta-amino acids, gamma-amino acids, delta-amino acids, and unnatural amino acids. Non-limiting examples of amino acids include alanine, valine, leucine, isoleucine, proline, phenylalanine, tryptophan, methionine, glycine, serine, threonine, cysteine, glutamine, asparagine, tyrosine, lysine, arginine, aspartic acid, glutamic acid, and combinations thereof. Cryobiology, 41(4):257-279 (2000).

Amino acid derivatives may also be used in the present compositions and methods. Non-limiting examples of amino acid derivatives include amino acid salts and amino acid solvates. Non-limiting examples of the amino acid salts include alkaline metal salts or alkaline earth metal salts such as sodium salts, potassium salts, and calcium salts; halogen acid salts such as hydrofluoric acid salts, hydrochloric acid salts, hydrobromic acid salts, and hydroiodic acid salts; inorganic acid salts such as nitrate salts, perchlorate salts, sulfate salts, and phosphate salts; and organic acid salts such as fumarate salts, succinate salts, citrate salts, oxalate salts, maleate salts, acetate salts, lactate salts, and ascorbate salts. Non-limiting examples of the amino acid solvates include hydrates, alcoholates (for example, methanolates, ethanolates), and etherates (for example, diethyl etherates).

In certain embodiments, the amino acid concentration in the present composition is 0.01-10.0% by weight, or 0.1-1.0% by weight.

DMSO

In certain embodiments, the present preservation composition is substantially free of dimethyl sulfoxide (DMSO), does not comprise DMSO, or is DMSO-free.

In certain embodiments, the present preservation composition comprises DMSO. In various embodiments, the concentration of DMSO is less than or equal to about 4% (v/v), less than or equal to about 3% (v/v), less than or equal to about 2% (v/v), less than or equal to about 1% (v/v), less than or equal to about 0.5% (v/v), less than or equal to about 0.1% (v/v), less than or equal to about 0.05% (v/v), less than or equal to about 0.02% (v/v), or less than or equal to about 0.01% (v/v).

Vitamins

In another embodiment, the preservation composition further comprises one or more vitamins. Non-limiting examples of vitamins include D-calcium pantothenate, choline chloride, folic acid, niacinamide, pyridoxine HCl, thiamine HCl, and riboflavin.

Salts

In certain embodiments, the present composition further comprises one or more salts, including inorganic salts, and/or organic salts. Non-limiting examples of inorganic salts include, potassium chloride, sodium bicarbonate, sodium chloride, and sodium phosphate monobasic, potassium phosphate monobasic, potassium phosphate dibasic, sodium bicarbonate, calcium chloride, magnesium chloride, potassium bicarbonate, potassium monophosphate, and combinations thereof.

In certain embodiments, the composition does not comprise serum. In certain embodiments, the composition does not comprise any raw materials of direct human or animal origin, or materials that have been produced using materials of human or animal origin.

In one embodiment, the present composition comprises a plurality of nanoparticles microparticle, nanotubes, or combinations thereof. Exemplary nanoparticles, microparticles, or nanotubes include carbon or noble metal (e.g., gold, silver, titanium, palladium, platinum, and copper) nanoparticles, microparticle, or nanotubes. Choi et al., Applied Physics Letter 79: 2252-2254, 2001; Eastman et al., Applied Physics Letter 78: 718-720, 2001.

The present preservation composition may comprise other optional components, including, but not limited to, peptides, other proteins, sugar alcohols, amino saccharides, glycoproteins, and alcohols, pH controlling agents, moisturizing agents, preservatives, viscosity controlling agents, or combinations thereof. U.S. Pat. No. 9,055,739.

Cryopreservation

The present disclosure provides for cryopreservation compositions and methods for cryopreserving biological materials.

The present method comprises contacting/combining the biological material (e.g., cells, tissues, an organ, viral particles) with a cryopreservation composition. In certain embodiment, this contacting/combining/mixing step involves adding the cryopreservation composition to the cells, and mixing the cells with the cryopreservation composition. This step of the present method (e.g., step (a)) may results in obtaining a mixture (e.g., a liquid mixture) of the cells in suspension in the medium.

The present disclosure provides a method of cryopreserving cells comprising the steps of placing cells in the cryopreservation composition, and cryopreserving the cells that are in the cryopreservation composition.

In certain embodiment, when cells are treated for cryopreservation, after the cells are suspended in the cryopreservation composition in a liquid state, the resulting suspension is frozen by maintaining it under conditions for cryopreservation. When the cells are needed, the frozen mixture of cells and the cryopreservation composition are subjected to a thawing process, after which the cells can be recovered.

In certain embodiment, to detach adherent or semi-adherent cells from a substrate (e.g., to form a cell suspension), cells are treated with an enzyme (e.g., a proteinase (e.g., trypsin). In certain embodiment, cells are detached from the culturing substrate (e.g., a cell culture dish, flask, etc.) by mechanically scraping the cells loose from the substrate. In certain embodiment, to detach adherent or semi-adherent cells from a substrate (e.g., to form a cell suspension), cells are treated with a chemical (e.g., a detergent). In certain embodiments, in the case of a chemical or enzymatic treatment, the cells are then centrifuged and washed in order to remove the enzyme or the detergent.

The cells and the cryopreservation composition can be physically combined according to a number of methods. In certain embodiments, the cells are present in a cell suspension prior to combination with the cryopreservation composition. In one embodiment, the step of combining the cells with the cryopreservation composition comprises providing the cells for cryopreservation in a cell suspension and adding the cryopreservation composition to the cell suspension (with or without mixing). In one embodiment, the step of combining the cells with the cryopreservation composition comprises providing the cells for cryopreservation in a cell suspension and adding the cell suspension to the cryopreservation composition (with or without mixing).

In certain embodiments, the cryopreservation medium may be added to the biological material (e.g., cells, tissues, an organ, viral particles) in step-wise increments of increasing concentration.

In certain embodiments, prior to cryopreservation, the cell culture medium is modified to include all the components needed for cryopreservation, and then the cells are removed from the culturing substrate (e.g., a cell culture dish, flask, etc.).

In certain embodiments, when or before being mixed/combined with the biological material, the temperature of the cryopreservation composition ranges from about 4° C. to about 45° C., from about 10° C. to about 40° C., from about 15° C. to about 40° C., from about 20° C. to about 40° C., from about 30° C. to about 40° C., from about 33° C. to about 38° C., or about 37° C.

In certain embodiments, the mixture of the cells and the cryopreservation medium is equilibrated prior to freezing the mixture. For example, the mixture is equilibrated for a time period ranging from about 10 seconds to about 1 hour, from about 20 seconds to about 50 minutes, from about 20 seconds to about 40 minutes, from about 30 seconds to about 30 minutes, from about 30 seconds to about 20 minutes, from about 30 seconds to about 10 minutes, from about 30 seconds to about 5 minutes, from about 30 seconds to about 2 minutes, from about 30 seconds to about 1 minute, from about 1 minute to about 40 minutes, from about 5 minutes to about 30 minutes, or from about 5 minutes to about 10 minutes.

In certain embodiments, prior to freezing the mixture the mixture of the cells and the cryopreservation medium is equilibrated at a temperature ranging from about 4° C. to about 45° C., from about 10° C. to about 40° C., from about 15° C. to about 40° C., from about 20° C. to about 40° C., from about 30° C. to about 40° C., from about 33° C. to about 38° C., or about 37° C.

In a further step, the present method compromises freezing the mixture of the biological material and the cryopreservation composition. In one embodiment, the mixture comprising the biological material is transferred to a freezing container, which is then transferred to subzero temperature. Suitable containers include, but are not limited to Mr. Frosty® freezing containers (Thermo Scientific). When placed in a freezer, such containers can help provide a fixed rate of cooling.

In certain embodiments, the present method comprises the steps of combining a biological material (e.g., cells, tissues, an organ, viral particles) with the present preservation composition, and subjecting the combined biological material and the present preservation composition to cryopreservation conditions. As used herein, "cryopreservation conditions" refers to any set of conditions typically recognized as useful in the art for cryopreserving cells. In one embodiment, cryopreservation conditions can refer to an environment providing a cryopreservation temperature, or a temperature sufficiently below 0° C. to slow or stop biological activity within a cell, including but not limited to biochemical reactions within the cell that would lead to cell death. In specific embodiments, a cryopreservation temperature comprises a temperature of at or below about 0° C., at or below about −20° C., at or below about −50° C., at or below about −60° C., at or below about −70° C., at or below about −80° C., at or below about −90° C., at or below about −100° C., at or below about −110° C., at or below about −120° C., at or below about −135° C., at or below about −196° C., or in liquid nitrogen.

As used herein, the term "cryopreserved state" means a state of being at a cryopreserved temperature.

Freeze-drying and cryopreservation in accordance with the present disclosure may be carried out in any method suitable to the biological material. The freezing of above methods of the present disclosure can be done in any method or apparatus known in the art.

In certain embodiments, the present method comprises slow-freezing of the biological material. In one embodiment, for the slow-freezing, the biological material is first cooled at a controlled rate to a temperature below −50° C., below −70° C., or to a temperature between −70° C. and −100° C.; optionally followed by further cooling of the biological material, e.g. by transfer of the biological material to liquid nitrogen ($N_2$). In certain embodiments, the controlled rate is a cooling rate between about −0.1° C./min and about −10° C./min, between about −0.2° C./min to about −5° C./min, or about 1° C./minute.

In certain embodiments, the freezing container having the cryopreservation composition with the biological material is placed at a temperature of between −70° C. and −100° C., or at −80° C. for a period of time (e.g., overnight). Thereafter, the container may be transferred to liquid nitrogen ($N_2$) at about −196° C.

In certain embodiments, the freezing container having the cryopreservation composition with the biological material is put at a temperature of between −70° C. and −100° C., or at −80° C. for a period of time (e.g., overnight). Thereafter, the container may be transferred to liquid nitrogen ($N_2$) at about −196° C.

In certain embodiments, the present method comprises vitrification of the biological material. In certain embodiments, the biological material in the cryopreservation composition is then cooled at a rate of about 30,000-about 100,000,000° C./minute, equal to or greater than about 50,000° C./minute, equal to or greater than about 100,000° C./minute, equal to or greater than about 200,000° C./minute, equal to or greater than about 350,000° C./minute, or equal to or greater than about 1,000,000° C./minute.

In certain embodiments, the biological material in the cryopreservation composition is exposed to a temperature less than or equal to −80° C. (e.g., dry ice), less than or equal to −100° C., −196° C. (e.g., liquid nitrogen), or −205° C. (e.g., slush nitrogen which is a mixture of liquid and solid nitrogen).

In certain embodiments, continuous temperature control may be provided during the cryopreservation or reanimation process. U.S. Pat. No. 9,485,984.

In one embodiment, the present method comprises a stepped method of cryopreserving cells that comprises cooling the cells to a first temperature, holding at that first temperature for a first period of time, then cooling the cells to a second temperature for storing the cells.

In one embodiment, the biological material (e.g., cells, viral particles, etc.) is suspended in the cryopreservation composition, the suspension thus prepared is dispensed into freezing tubes (e.g., cryotubes, cryovials, etc.), and the resulting tubes are placed directly in an ultra-low temperature freezer (e.g., at −80° C.) to freeze the biological material. In one embodiment, the biological material in the cryopreservation composition is frozen directly in a freezer at −80° C.

In some embodiments, parameters of the freezing step and/or thawing step are optimized such that temperature ramp-up and/or ramp-down rates do not disrupt the integrity of the biological material, and does not adversely affect the viability or function of the biological material post-thaw.

In some embodiments, a biological material in the cryopreservation composition is cooled in a temperature ramp-down phase having a selected rate of temperature reduction. In some embodiments, a rate of temperature reduction in a temperature ramp-down phase is about 10° C. per minute, about 1° C. per minute, about 2° C. per minute, about 5° C. per minute, about 7° C. per minute, about 12° C. per minute, about 15° C. per minute, about 17° C. per minute, about 20° C. per minute, or rates within the values above. In some embodiments, a temperature ramp-down phase may include cooling the biological material at a rate of approximately 10° C. per 10 seconds, 10° C. per 20 seconds, 10° C. per 30 seconds, 10° C. per 40 seconds, 10° C. per 50 seconds, 10° C. per 60 seconds, 10° C. per 70 seconds, 10° C. per 80 seconds, 10° C. per 90 seconds, 10° C. per 100 seconds, 10° C. per 110 seconds, 10° C. per 120 seconds, 10° C. per 130 seconds, 10° C. per 140 seconds, 10° C. per 150 seconds, 10° C. per 160 seconds, 10° C. per 170 seconds, 10° C. per 180 seconds, 1° C. per 190 seconds, or 10° C. per 200 seconds.

In certain embodiments, a temperature ramp-down phase may include a flash freezing (e.g., maximal temperature reduction) step.

In certain embodiments, the freezing step of the present method comprises non-linear cooling. The non-linear cooling cryopreservation protocol can be executed using a bulk freezing unit or a cryomicroscopy apparatus or other suitable apparatus, including one with a programmable thermocycler, that can be programmed to cool cells according to a pre-determined cooling profile.

In one embodiment, the freezing step of the present method comprises cooling the biological material to a first temperature for a first period of time, then cooling the cells to a second temperature for storing the cells. In one embodiment, the cells are cooled to a temperature between about −3° C. and −30° C., held at that temperature for 1 to 30 minutes, then cooled to a temperature below −60° C. to store the cells. U.S. Pat. No. 9,078,429.

In one embodiment, the method comprises placing the cells in a cryopreservation composition and allowing the composition to achieve a starting temperature of 4° C. Once the compositions comprising the cells achieve the starting temperature, they are kept at that temperature for about 15 minutes. The cells are then cooled at a rate of about −1° C./min until the cell composition achieves a temperature of about −3° C.

In one embodiment, the method comprises placing the cells in a cryopreservation composition and allowing the composition to achieve a starting temperature of 4° C. The cells are then cooled at a rate of 1° C./min between 4° C. and −45° C. Then, once the composition is at a temperature of about −45° C., the composition is further cooled until the cell composition achieves a storage temperature of about −120° C.

In one embodiment, the cell suspension in the cryopreservation is distributed into cryotubes or cryovials etc., which are then placed in a freezing container. The freezing container is transferred to 4° C. for about 1 hour, and then placed in a chamber at about −80° C. for at least 12 hours, or at least 24 hours. The cryotubes are then stored in liquid nitrogen.

In some embodiments, the biological material is optionally subjected to an intermediate storing temperature for a desired period of time. The intermediate storing temperature may range from about 0° C. to about −100° C., from about −50° C. to about −60° C., from about −60° C. to about −70° C., from about −70° C. to about −80° C., from about −80° C. to about −90° C., from about −90° C. to about −100° C., and overlapping ranges thereof.

In some embodiments, the biological material is stored at an intermediate storing temperature for a period of time before transfer to longer term storage. For example, the cells may be maintained at an intermediate storing temperature overnight, or any other suitable period of time, before being transferred to liquid nitrogen for long term storage. Other temperatures may be used in other embodiments (e.g., storage at −20° C., −30° C., −40° C., −50° C., −60° C., etc.) In several embodiments, a multi-step "step-down" procedure with multiple (2, 3, 4, 5 or more) intermediate storing temperatures is used.

The freezing of the biological material in the cryopreservation composition may be done using a programmed freezer. The freezing of the biological material in the cryopreservation composition may be done without using a programmed freezer.

The freezing may be directional freezing, stationary freezing, and the like.

Non-limiting examples of the freezing methods include using a directional freezing device, using a mechanical freezer, using a stepwise freezing apparatus, slush freezing, freezing in cryogenic fluid, freezing in controlled rate freezers, using a liquid bath freezer, using a cold air freezer, etc. U.S. Pat. Nos. 5,827,741 and 6,723,497.

Any freezing apparatus capable of providing prolonged sub-zero temperatures to maintain a cryopreserved state may be used. Freezing and storage may be carried out in the same apparatus, or a first freezing apparatus may be used prior to transfer of frozen samples to a long-term storage apparatus. In one embodiment, liquid nitrogen storage vessels are used. In certain embodiments, passive freezing methods involving more sophisticated cooling devices, such as the programmable, rate controlled Planer freezers (Planer Products) are used. U.S. Pat. No. 8,512,941.

The biological material in the cryopreservation composition may be stored in a cryopreserved state for any length of time until they are needed. When the cells are at the storage temperature, they may be stored for a desired period, such as about 1-5 hours, about 5-12 hours, about 12-24 hours, about 24-48 hours, about 48 hours, about 1 week, about 2 weeks, about 3 weeks, about 1 month, about 2 months, about 3 months, about 6 months, about 1 year, about 2 years, about 3 years, about 4 years, about 5 years, or longer. U.S. Patent Publication No. 20170202212.

Thawing

The appropriate storage conditions for preserving a biological material may comprise any such conditions that maintain the biological material viable. Such conditions can include a cryopreservation temperature of at or below about 0° C., at or below about −20° C., at or below about −50° C., at or below about −60° C., at or below about −70° C., at or below about −80° C., at or below about −90° C., at or below about −100° C., at or below about −110° C., at or below about −120° C., at or below about −135° C., at or below about −196° C., or in liquid nitrogen. For hypothermic preservation, the temperature can be between 8° C. and 0° C. In the case of lyophilized samples, the temperature may be any temperature above 0° C. (e.g., room temperature, an ambient temperature, etc.) or below 0° C., as long as, the material is kept away from humidity.

The biological material can remain in a preserved state (e.g., a cryopreserved state) for periods of days, weeks, months or years, until the biological material is required. When required, the cryopreserved biological material is retrieved and thawed.

In certain embodiments, the present method further comprises the step of thawing the frozen composition, more particularly under conditions that maintain cell viability.

In certain embodiments, the biological material in the cryopreservation composition is thawed in a water bath (e.g., by placing the cryotube or cryovial in a water bath), at a temperature at or below about 42° C., from about 10° C. to about 40° C., from about 20° C. to about 37° C., room temperature, or about 37° C.

In one embodiment, the biological material in the cryopreservation composition is thawed in a water bath at about 37° C. Optionally, it would be then moved to a lower temperature such as 4° C. or on ice.

In certain embodiments, a "step up" thawing process having a step up heating rate (or a temperature ramp-up heating rate) is used. For example, the cryovial may be placed in sequential storage environments with increasing temperatures before being transferred to a temperature that is around body temperature, for example a water bath having a temperature of around 37° C., or any other suitable temperature.

In certain embodiments, the cryopreserved biological material in the cryopreservation composition is thawed at a warming rate ranging from about 5° C./min to about 80° C./min, from about 10° C./min to about 70° C./min, from about 10° C./min to about 60° C./min, from about 10° C./min to about 50° C./min, from about 10° C./min to about 40° C./min, from about 10° C./min to about 30° C./min, about 10° C./min to about 20° C./min, from about 20° C./min to about 40° C./min, greater than about 20° C./min, greater than about 25° C./min, greater than about 30° C./min, greater than about 35° C./min, greater than about 40° C./min, or about 30° C./min.

In certain embodiments, after thawing, the biological material is washed, suspended in the appropriate media and treated as needed for use in research or clinical applications.

In certain embodiments, after thawing, the cells are transferred to a culture dish for re-culturing. The cells may be cultured under appropriate conditions for a period of about 30 minutes, about 1 hour, about 6 hours, about 12 hours, about 24 hours, about 48 hours, about 72 hours, about 86 hours, about 110 hours, about 1 week, about 2 weeks, or more than 3 weeks prior to research or clinical applications. U.S. Patent Publication No. 20170196221.

In certain embodiments, resuscitated adherent cells or semi-adherent cells are re-cultured immediately upon thawing. The resuscitated cells are thus provided a recovery time to overcome damage inflicted, e.g., during removal from culture prior to cryopreservation.

In certain embodiments, after thawing, the biological material is used in vivo without an intervening culturing step.

In certain embodiments, after thawing, the cells may be re-suspended in a fluid or other medium suitable for the intended use. For example, the cells can be re-suspended in any osmotically supportive solution. In certain embodiments, the cells can be re-suspended in a physiologically compatible buffer, such as the buffer solutions described herein. Preferably, any physiologically compatible material providing a composition for convenient delivery in vivo can be used to re-suspend the cells.

Viability of Cryopreserved Cells

The present compositions and methods may allow for the preservation (e.g., cryopreservation) of cells, wherein the cells maintain a good viability after recovery. Preservation may be ceased using many different processes that can be chosen to suit the method of preservation and the nature of the biological material, including raising the temperature of the biological material, hydration of lyophilized biological material and/or removal of solutes.

As used herein, the term "viability" refers to the percentage of viable biological material (such as cells, e.g., based on the presence of DNA and/or an intact cell membrane system, or viable viruses). In certain embodiments, viable biological material refers to a biological material comprising some viable cells or fractions of cells that are metabolically active or would become metabolically active after their release from the preservation state.

In certain embodiments, the post-thaw viability of the biological material (e.g., cells or viruses) is at least about 50%, at least about 55%, at least about 60%, at least about 65%, at least about 70%, at least about 75%, at least about 80%, at least about 85%, at least about 90%, or at least about 95%.

In certain embodiments, the present compositions and methods ensure that the cells display a limited amount of, or minimal, necrosis and apoptosis after thawing. In certain embodiments, necrosis and/or apoptosis is observed in less than about 25%, less than about 20%, less than about 15%, less than about 10%, less than about 5%, or less than about 1% of the cells.

The viability can be measured by any methods known in the art. In certain embodiments, the viability is measured using a Trypan blue internalization test or by measuring propidium iodide uptake. In certain embodiments, the viability is measured by assaying the ability of cells to attach efficiently (e.g., the attachment assays). In certain embodiments, proliferation assays can be used to determine if the attached cells can proliferate as expected after cryopreservation. Attachment and proliferation efficiency can be compared to control cells which have not undergone cryopreservation.

There are various tests known in the art to determine the viability and function of the cells. In certain embodiments, these tests are dependent on the cell type and the desired use of the cell.

For stem cells or progenitor cells, the methods described herein may further ensure that the cells maintain their pluripotency. This can be established by the determination of expression of lineage-specific markers. For instance, functional characterization of the mesenchymal stem cells may include induction of adipogenic, osteogenic and chondrogenic differentiation in vitro using commercially available differentiation kits and RT-PCR to detect lineage specific expression of mRNA, indicative for adipogenic, osteogenic and chondrogenic differentiation potential. Similarly, the quality of the undifferentiated stem cells can be tested by isolation of mRNA and testing on cell-specific markers. In particular embodiments, the ability to differentiate into a cell of the specified lineage is maintained, i.e., does not significantly differ from unprocessed cells. The pluripotency of the embryonic stem (ES) cells can be tested using art known methods, including, for example, Oct4-GFP expression, elevated alkaline phosphatase expression, and SSEA-1 surface glycoprotein expression. Several in vitro methods can be applied to assess stem cell recovery after experimental treatment. These assessments may include, but are not limited to, membrane integrity, metabolic and other functional assays and/or colony growth in culture, and fluorescent assays, such as SYTO/EB. In certain embodiments, differentiation tests, immunophenotype characterization, and/or an inspection of the morphology may be used to assay stem cells and/or progenitor cells.

For cryopreservation of zygotes, cleavage rates can be determined after cryopreservation and compared to control groups to determine if there has been any cellular damage during the cryopreservation process. The viability of oocytes can be determined by examination of the morphological characteristics of the cells following cryopreservation. Morphologically viable oocytes exhibit intact zona pellucida and plasma membrane and refractive cytoplasm, while nonviable oocytes appear degenerated when visualized under a light microscope. The ultimate criterion for oocyte viability and function is their capability to be fertilized by healthy sperm in vitro and in vivo, followed by cleavage, blastocyst, and/or hatching or development of the fetus. U.S. Pat. No. 9,538,745.

In certain embodiments, the present preservation compositions and methods, as well as the biological material recovered from preservation using the present preservation compositions and methods can be used for research and/or clinical application (e.g., cell-based therapies, transplantation, regenerative medicine, diagnostics and genetic testing, cell/tissue banking for surveillance, toxicity testing and for in vitro fertilization).

Biological Materials

The term "biological material" denotes cells, cell aggregates, tissue, organs, biological fluids, viral particles, and any other membranous entity such as liposomes (natural or synthetic).

Any type of cells or tissues may be preserved using the present compositions and methods.

In certain embodiments, the cells are mammalian cells, including, but not limited to, human cells, murine cells, porcine cells, canine cells, equine cells and bovine cells. The cells may be from a mammal that is of an endangered or threatened species. The cells may be from a human or non-human mammal, for example Cercopithecoidea family, Hominoidea superfamily, *Canis familiaris, Felis catus, Cricetidae* spp., *Equus* spp. (e.g., *Equus caballus, Equus assinus*), Equidae family, *Bos taurus, Bos indicus,* Bovidae family, Camelidae family, *Bubalus bubalis, Capra aegagrus hircus,* Cervidae family, Cervinae family, *Ovis aries, Ovis canadensis, Capra hircus, Sus scrofa domestica, Mesocricetus* spp., *Mustela vison, Cavia porcellus, Meriones unguiculatus, Chinchilla laniger, Rattus norvegicus, Rattus* spp., *Mus musculus,* Leporidae family, *Oryctolagus cuniculus, Kobus* spp., *Gallus* spp., *Meleagria gallopavo,* Anatidae spp., *Mustela putorius, Columba domestica, Columba livia, Numida meleagris, Ornithorhynchus anatinus, Pavo cristatus, Bison* spp., *Struthio* spp., *Lama glama, Rhea* spp., *Dromiceius* spp., *Lama pacos, Rangifer tarandus, Bos grun-*

*niens, Camelus bactrianus, Camelus dromedarius*), and any endangered or threatened species.

The present compositions and methods may be used to preserve microorganisms, bacteria, non-mammalian animal cells (e.g., insect cells, avian cells, fish cells, etc.), or plant cells.

Non-limiting examples of the cell include stem cells, progenitor cells, embryos, sperm, oocytes, gametocytes, and zygotes.

The cells may be tumor cells or non-tumor cells. In one embodiment, the cells are fibroblasts.

Biological materials may comprise, without limitation, any of the following: fibroblasts, stem cells, progenitor cells, whole blood or fractions thereof, red blood cells, white blood cells, umbilical cord blood or fractions thereof, umbilical cord blood cells, bone marrow, oocytes, sperm, ova, embryos, cartilage, ovary, heart, skin, kidney, liver, lung. In addition, such biological material may comprise cellular organisms, which may be eukaryotes or prokaryotes, including bacteria, and yeast, etc. Additionally, biological material may also comprise whole multi-cellular organisms that are capable of surviving cryopreservation such as nematodes. Fractions of blood may comprise any fraction of blood comprising blood cells (white and/or red), plasma and/or solutes and/or sub-cellular components (e.g. fractions of cells, such as platelets, components of degraded cells, etc.), proteins, lipids, antibodies, etc.

The present compositions and methods may be used to preserve any types of cells, including but not limited to, cellular materials derived from tissues and organs, including, but not limited to, pancreatic islet cells, chondrocytes, cells of neural origin, cells of hepatic origin, cells of opthalmolic origin, cells of orthopedic origin, cells from connective tissues, and cells of reproductive origin, and cells of cardiac and cardiovascular origin.

Stem cells include adult stem cells, embryonic stem cells, induced pluripotent stem cells (iPSCs), peripheral blood stem cells, umbilical cord blood stem cells, mesenchymal stem cells, stem cells derived from tissues and organs or other sources, including fetal and/or embryonic sources, as well as mixtures of stem cells with other cells and from different sources. Adult stem cells include bone marrow stem cells, hematopoietic stem cells, skin stem cells, ocular stem cells, neural stem cells, cardiac stem cells, etc.

In certain embodiments, the stem cells of endodermal origin are pulmonary epithelial stem cells, gastrointestinal tract stem cells, pancreatic stem cells or hepatic oval cells and/or progenitor cells thereof. In particular embodiments, the cells of urogenital origin are either categorized as mammary and prostatic gland stem cells or ovarian and testicular stem cells and/or progenitor cells thereof. In particular embodiments, the cells of mesodermal origin are bone marrow cells, hematopoietic stem cells, stromal stem cells or cardiac stem cells and/or progenitor cells thereof. In particular embodiments, the cells of ectodermal origin are neural stem cells, skin stem cells or ocular stem cells and/or progenitor cells thereof.

Cell types that may be cryopreserved using the compositions and methods of the present disclosure include, for example, differentiated cells, such as fibroblasts, epithelial cells, cardiomyocytes, hepatocytes, neural cells, epidermal cells, keratinocytes, hematopoietic cells, melanocytes, chondrocytes, B-cells, T-cells, erythrocytes, macrophages, monocytes, or muscle cells; and undifferentiated cells, such as embryonic, mesenchymal, or adult stem cells. The cells can be haploid, diploid, or tetraploid. Other cells include cells from the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

In further particular embodiments, the cells are obtained from adult brain, bone marrow, blood vessels, skeletal muscle, skin, teeth, heart, gut, liver, or other adult tissues. In particular embodiments, the cells are selected from the group consisting of endodermal, urogenital, mesodermal or ectodermal origin.

Tissues include cornea, cartilage, bone, skin, heart valves, Islets of Langerhans, embryos from humans, animals, fish, shellfish and plants, and ovarian tissues from humans and animals. The present compositions and methods may also preserve engineered tissues and tissue constructs.

In certain embodiments, the present compositions and methods can be used to cryopreserve oocytes or sperm in assisted reproductive technology, or for patients undergoing chemotherapy or radiation therapy. The method can also be used for the cryopreservation of stem cells, which can then be used as the basis of stem cell-based therapies, cell transplantation, tissue engineering, and regenerative medicine. The method can also be used to cryopreserve oocytes or sperm from an animal that is rare or at risk of becoming extinct for future use in assisted reproductive technologies for the preservation of the species. The method can further be used for animal husbandry purposes (e.g., the breeding and raising of animals), for example, for the cryopreservation of embryonic stem cells, gametocytes, oocytes, or sperm from animals such as cows, pigs, and sheep.

Cryopreserved cells are useful for the treatment of a variety of diseases. For example, in several embodiments, ocular cells are used to treat ocular diseases including, but not limited to age related macular degeneration (wet or dry), diabetic macular edema, idiopathic choroidal neovascularization, or high myopia macular degeneration. In some ocular embodiments, RPE cells are used. In several embodiments, cardiac stem cells are used to treat cardiovascular disorders such as myocardial infarction, ischemic cardiac tissue damage, congestive heart failure, aneurysm, atherosclerosis-induced events, cerebrovascular accident (stroke), and coronary artery disease. In several embodiments, liver stem cells are used to treat liver disease such as hepatitis, cirrhosis, cancer, and the like. Diseases in other tissues, such as the kidney, lung, pancreas, intestine, bone and/or cartilage, and neural tissues, among others, may be treated with the methods and devices disclosed herein. In some embodiments, harvested bone marrow stem cells may be used to repopulate hematopoietic cells that are reduced due to leukemias, cancers, or therapies that reduce blood cell counts.

The present disclosure is also useful in various methods of treatment. Cellular therapy, or cell therapy, can generally encompass transplantation of human or animal cells to replace or repair damaged tissue and/or cells. Cell therapy has been used to rebuild damaged cartilage in joints, repair spinal cord injuries, strengthen a weakened immune system, treat autoimmune diseases, and help patients with neurological disorders such as Alzheimer's disease, Parkinson's disease, and epilepsy. Further uses have included treatment of a wide range of chronic conditions such as arteriosclerosis, congenital defects, and sexual dysfunction.

Cell therapy typically involves the injection of either whole cells or cell extracts that are xenogenic, allogenic (from another human donor), or autologous (wherein the cells are extracted from and transplanted back into the same patient).

The present compositions and methods can be used in applications where it is useful to store cells for a period of time for use in later cell therapies. This can include storage of a patient's own cells for later transplantation, as well as storage of a generic cell line (for example, an embryonic stem cell line for use in research or therapies).

Viruses or viral particles can be any viruses. In certain embodiments, the viruses or viral particles comprises adenoviruses, adeno-associated viruses, retroviruses, herpes viruses and the like. In certain embodiments, the viruses or viral particles are those which may be used in gene therapy.

Kits

The present disclosure also provides for a kit comprising the present preservation composition (in solid or liquid form as described herein). Such kits may include one or more containers comprising present preservation composition. In one embodiment, the kit comprises the present preservation composition which comprises a biological material. In one embodiment, the kit comprises the biological material for preservation (e.g., cryopreservation).

In some embodiments, the kit can comprise instructions for use in any of the methods described herein. In one embodiment, the kit comprises instructions for preservation of biological materials using the preservation composition and method. The kit may further comprise a description of selecting a subject suitable for treatment based on identifying whether the subject is in need of the treatment. In some embodiments, the instructions comprise a description of administering the thawed biological material after cryopreservation to a subject who is in need of the treatment. In certain embodiments, instructions supplied in the kits are written instructions on a label or package insert. The label or package insert may also indicate clinical and/or research applications of the biological material.

Parts of a kit may be used simultaneously or chronologically staggered, i.e., at different points in time and with equal or different time intervals for any component of a kit. Time intervals can be selected to obtain the desired effect.

The kits provided herein are in suitable packaging. Suitable packaging includes, but is not limited to, a vial (e.g., a cryovial), a bottle, an ampoule, a tube (e.g., a cryotube), a bag, a flask, a jar, flexible packaging, and the like. Also contemplated are packages for use in combination with a specific device, such as a freezing container, a cryovial and/or a cryotube.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

The following are examples of the present invention and are not to be construed as limiting.

Example 1

Freezing Solution Preparation 9 stock samples of the freezing solution were prepared (Table 1). Albumin was HSA purchased from Kedrion. Gelatin was purchased from Gelita (gelatin was prepared from bovine hides; Batch No. L600217) or Nippi (gelatin was prepared from bovine, swine and/or fish, etc.; Lot No. S150806). Trehalose was purchased from Hayashibara. Sucrose was purchased from J. T. Baker. Glycerol was purchased from Spectrum. PEG was purchased from SIGMA. The percentages of the various components in the tables of the Examples are % (w/v).

In these experiments, the stock freezing solutions were formulated by dissolving the desired agents in DMEM at a concentration that was two folds of a desired working concentration. Thus, after mixing with the cell suspension at a 1:1 volume ratio, the desired working concentration can be obtained. Likewise, a stock freezing solution having 3-fold, 4-fold, or 5-fold concentration of the desired working concentration can also be prepared if needed.

TABLE 1

2X Stock freezing solutions

| | Macromolecule | | Sugar | | Permeating Cryoprotectant | | Solvent |
|---|---|---|---|---|---|---|---|
| | Albumin | Gelatin | Trehalose | Sucrose | Glycerol | PEG | |
| CPA-1 | 2% | — | 0.2M | — | 10% | — | DMEM |
| CPA-2 | 10% | — | 1.0M | — | 20% | — | DMEM |
| CPA-3 | 4% | — | 0.4M | — | 30% | — | DMEM |
| CPA-4 | 4% | — | — | 0.6M | 20% | — | DMEM |
| CPA-5 | 10% | — | — | 0.2M | 40% | — | DMEM |
| CPA-6 | — | 8% | 0.4M | — | — | 5% | DMEM |
| CPA-7 | — | 2% | 0.2M | — | — | 20% | DMEM |
| CPA-8 | — | 2% | — | 0.6M | — | 4% | DMEM |
| CPA-9 | — | 6% | — | 0.8M | — | 10% | DMEM |

Freezing Cells

Fibroblast cells were cultured and expanded for five days. After cells reached about 80-90% confluency, the cells were trypsinized and suspended in DMEM. 500 μl of the cell suspension ($10^6$ cells/mL) was mixed with 500 μl of the 2× stock freezing solution in cryotubes. In CPA-1 to CPA-9 (different samples), the final concentration (working concentration) of each component of the freezing solution is shown in Table 2. The control sample contains DMEM.

TABLE 2

Working concentrations of the components of the freezing solutions

| | Macromolecules | | Sugar | | Permeating Cryoprotectant | | Solvent |
|---|---|---|---|---|---|---|---|
| | Albumin | Gelatin | Trehalose | Sucrose | Glycerol | PEG | |
| CPA-1 | 1% | — | 0.1M | — | 5% | — | DMEM |
| CPA-2 | 5% | — | 0.5M | — | 10% | — | DMEM |
| CPA-3 | 2% | — | 0.2M | — | 15% | — | DMEM |
| CPA-4 | 2% | — | — | 0.3M | 10% | — | DMEM |
| CPA-5 | 5% | — | — | 0.1M | 20% | — | DMEM |
| CPA-6 | — | 4% | 0.2M | — | — | 2.5% | DMEM |
| CPA-7 | — | 1% | 0.1M | — | — | 10% | DMEM |
| CPA-8 | — | 1% | — | 0.3M | — | 2% | DMEM |
| CPA-9 | — | 3% | — | 0.4M | — | 5% | DMEM |
| Control | | | | DMEM | | | |

The cryotubes were then transferred to a freezing container containing isopropanol (e.g., Nalgene® Mr. Frosty), and stored at a −80° C. freezer for 1-2 days. Subsequently, these cryotubes were transferred from the −80° C. freezer to liquid nitrogen storage tank for long term storage.

Cell Viability Test

The cryotubes were placed in a 37° C. water bath for 2-3 min to thaw the cryopreserved cells. The thawed cell suspensions were mixed gently and the viability of cells was analyzed by ADAM-MC Automatic Cell Counter (Digital Bio).

Results

Figure 1:
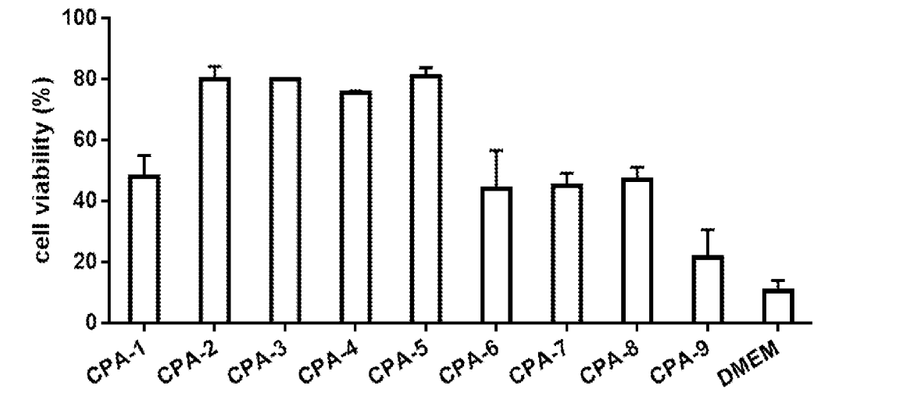
FIG. 1 shows post-thaw cell viabilities after using different cryopreservation compositions CPA-1 to CPA-9 (see Example 1). DMEM was used as a control.

The viabilities of the fibroblast cells in various cell freezing solutions are shown in Table 3 and FIG. 1. The cells that were cryopreserved in the cryopreservation composition containing a macromolecule, a sugar, and a permeating cryoprotectant maintained higher viabilities than that in DMEM alone.

TABLE 3

Post-thaw viability of cells

|  | Cell viability (%) ||
|---|---|---|
|  | Sample 1 | Sample 2 |
| CPA-1 | 43 | 53 |
| CPA-2 | 77 | 83 |
| CPA-3 | 80 | 80 |
| CPA-4 | 75 | 76 |
| CPA-5 | 79 | 83 |
| CPA-6 | 53 | 35 |
| CPA-7 | 42 | 48 |
| CPA-8 | 50 | 44 |
| CPA-9 | 15 | 28 |
| Control | 8 | 13 |

Example 2

In order to test the effects of various components of the cryopreservation solution on cell viabilities, different samples were prepared according to Table 4.

TABLE 4

| Components (concentration) | Group I | Group II | Group III |
|---|---|---|---|
| Permeating Cryoprotectant (2-40%) | — | V | V |
| Sugars (0.1-1M) | V | — | V |
| Macromolecules (1-10%) | V | V | — |
| Cells | $10^5$ and $10^7$ cells/mL |||

27 cryopreservation compositions were prepared according to Table 7, including 9 Group I cryopreservation compositions, 9 Group II cryopreservation compositions, and 9 Group III cryopreservation compositions.

Expansion of Cells Prior to Cryopreservation

Two tubes of FE002-SK2 cells (passage 9; P9), which are fetal skin fibroblast cells, were thawed with the following viability (Table 5).

TABLE 5

|  | Total cells (cell/mL) | Non-viable cells (cell/mL) | Viable cells (cell/mL) | Viability (%) |
|---|---|---|---|---|
| Tube-1 | $2.11 \times 10^6$ | $2.37 \times 10^5$ | $1.87 \times 10^6$ | 88 |
| Tube-2 | $1.84 \times 10^6$ | $2.09 \times 10^5$ | $1.63 \times 10^6$ | 88 |

The cells from the two tubes were combined, and distributed evenly to five T150 cell culture flasks (about 4,666 cells/cm$^2$). 20 mL cell culture media were added to the cell culture flasks to culture the cells.

Harvesting Cells

About 7 days after seeding, the cells were harvested with the following viability (Table 6).

TABLE 6

|  | Total cells (cell/mL) | Non-viable cells (cell/mL) | Viable cells (cell/mL) | Viability (%) |
|---|---|---|---|---|
| Dilute 5 folds | $1.17 \times 10^6$ | $8.54 \times 10^4$ | $1.08 \times 10^6$ | 92 |

Before the 5-fold dilution, the original cell concentration was $1.08 \times 10^6 \times 5 = 5.4 \times 10^6$ cells/ml. The total cell suspension was 5.8 mL. 2 mL cell culture medium was added to the cells. Thus, the cell concentration was diluted to $4 \times 10^6$ cells/mL. The total cell suspension was 7.8 mL.

200 μL of the cell suspension was added to 200 μL each of the 2× cryopreservation compositions (Table 7) in a cryotube. The cell concentration was $2 \times 10^6$ cells/0.4 mL.

The cryotubes having the cryopreservation composition and cell mixture were placed in Mr. Frosty® freezing container which was then placed in a −80° C. freezer overnight. The cryotubes were transferred to a liquid nitrogen tank for long term storage.

Post-Thaw Cell Viability

The cryotubes were placed in a 37° C. water bath to thaw the cells. The viability of the cells was analyzed by the ADAM-MC Automatic Cell Counter (Digital Bio). Briefly, one cryotube was thawed each time, and the mixture was pipetted five times to mix. 20 μL of the mixture was mixed with 20 μL staining solution, and counted using the cell counter.

TABLE 7

Cryopreservation compositions and post-thaw cell viability

|  |  | Macromolecules | Sugars | Permeating Cryoprotectant | Cell viability (Mean ± SD) |
|---|---|---|---|---|---|
| Group I | CPA-1 | Albumin (1%) | Trehalose (0.1M) | — | 21.5 ± 2.10 |
|  | CPA-2 | Albumin (5%) | Trehalose (0.5M) | — | 72.0 ± 1.40 |
|  | CPA-3 | Albumin (2%) | Trehalose (0.2M) | — | 29.5 ± 7.80 |
|  | CPA-4 | Albumin (2%) | Sucrose (0.3M) | — | 47.5 ± 3.50 |
|  | CPA-5 | Albumin (5%) | Sucrose (0.1M) | — | 25.0 ± 11.3 |
|  | CPA-6 | Gelatin (4%) | Trehalose (0.2M) | — | 31.5 ± 13.4 |
|  | CPA-7 | Gelatin (1%) | Trehalose (0.1M) | — | 27 ± 7.1 |
|  | CPA-8 | Gelatin (1%) | Sucrose (0.3M) | — | 46 ± 7.1 |
|  | CPA-9 | Gelatin (3%) | Sucrose (0.4M) | — | 36.5 ± 6.4 |
| Group II | CPA-10 | Albumin (1%) | — | Glycerol (5%) | 3.5 ± 2.1 |
|  | CPA-11 | Albumin (5%) | — | Glycerol (10%) | 41 ± 8.5 |
|  | CPA-12 | Albumin (2%) | — | Glycerol (15%) | 50.5 ± 6.4 |
|  | CPA-13 | Albumin (2%) | — | Glycerol (10%) | 28.5 ± 0.7 |
|  | CPA-14 | Albumin (5%) | — | Glycerol (20%) | 50.5 ± 3.5 |
|  | CPA-15 | Gelatin (4%) | — | PEG (2.5%) | 39 ± 12.7 |
|  | CPA-16 | Gelatin (1%) | — | PEG (10%) | 61 ± 1.4 |

TABLE 7-continued

Cryopreservation compositions and post-thaw cell viability

|  |  | Macromolecules | Sugars | Permeating Cryoprotectant | Cell viability (Mean ± SD) |
|---|---|---|---|---|---|
|  | CPA-17 | Gelatin (1%) | — | PEG (2%) | 1.5 ± 2.1 |
|  | CPA-18 | Gelatin (3%) | — | PEG (5%) | 36.5 ± 46.0 |
| Group III | CPA-19 | — | Trehalose (0.1M) | Glycerol (5%) | 26 ± 4.2 |
|  | CPA-20 | — | Trehalose (0.5M) | Glycerol (10%) | 51 ± 12.7 |
|  | CPA-21 | — | Trehalose (0.2M) | Glycerol (15%) | 43.5 ± 14.8 |
|  | CPA-22 | — | Sucrose (0.3M) | Glycerol (10%) | 59 ± 8.5 |
|  | CPA-23 | — | Sucrose (0.4M) | Glycerol (20%) | 32.5 ± 12.0 |
|  | CPA-24 | — | Trehalose (0.2M) | PEG (2.5%) | 47.5 ± 4.9 |
|  | CPA-25 | — | Trehalose (0.1M) | PEG (10%) | 66 ± 8.5 |
|  | CPA-26 | — | Sucrose (0.3M) | PEG (2%) | 42 ± 7.1 |
|  | CPA-27 | — | Sucrose (0.4M) | PEG (5%) | 14.5 ± 7.8 |
| Control | DMSO-CPA | DMSO: 10% (v/v), FBS: 45% (v/v), DMEM: 45% (v/v) | | | 80.5 ± 0.7 |
|  | Complete-CPA | Trehalose: 0.2M, HSA: 0.025 g/mL, Glycerol: 17% (w/v) | | | 83 ± 1.4 |

In the Examples, "Complete-CPA", "Complete-1" or "Complete-2" refers to a cryopreservation composition containing a permeating cryoprotectant (e.g., glycerol), a saccharide (e.g., trehalose), and a macromolecule (e.g., HSA). They are embodiments of the present cryopreservation composition. "SD" refers to standard deviation. "Avg." refers to average values.

The raw data of the experiments are presented in Table 8.

TABLE 8

|  | Total cells (×$10^6$ cells/mL) | Non-viable cells (×$10^6$ cells/mL) | Viable cells (×$10^5$ cells/mL) | Cell viability (%) | Avg. | SD | Cell viability (mean ± SD) |
|---|---|---|---|---|---|---|---|
| DMSO-1 | 2.26E6 | 0.43E6 | 1.83E6 | 80 | 80.5 | 0.7 | 80.5 ± 0.7 |
| DMSO-2 | 2.23E6 | 0.42E6 | 1.81E6 | 81 |  |  |  |
| Complete-1 | 2.64E6 | 0.42E6 | 2.23E6 | 84 | 83 | 1.4 | 83 ± 1.4 |
| Complete-2 | 2.30E6 | 0.40E6 | 1.89E6 | 82 |  |  |  |
| CPA-1-1 | 2.40E6 | 1.84E6 | 0.56E6 | 23 | 21.5 | 2.1 | 21.5 ± 2.1 |
| CPA-1-2 | 2.41E6 | 1.90E6 | 0.50E6 | 20 |  |  |  |
| CPA-2-1 | 2.42E6 | 0.65E6 | 1.76E6 | 73 | 72 | 1.4 | 72 ± 1.4 |
| CPA-2-2 | 2.54E6 | 0.72E6 | 1.83E6 | 71 |  |  |  |
| CPA-3-1 | 2.41E6 | 1.56E6 | 0.85E6 | 35 | 29.5 | 7.8 | 29.5 ± 7.8 |
| CPA-3-2 | 2.52E6 | 1.91E6 | 0.62E6 | 24 |  |  |  |
| CPA-4-1 | 2.38E6 | 1.17E6 | 1.20E6 | 50 | 47.5 | 3.5 | 47.5 ± 3.5 |
| CPA-4-2 | 2.43E6 | 1.33E6 | 1.09E6 | 45 |  |  |  |
| CPA-5-1 | 2.40E6 | 1.61E6 | 0.80E6 | 33 | 25 | 11.3 | 25 ± 11.3 |
| CPA-5-2 | 2.12E6 | 1.75E6 | 0.37E6 | 17 |  |  |  |
| CPA-6-1 | 2.53E6 | 1.48E6 | 1.05E6 | 41 | 31.5 | 13.4 | 31.5 ± 13.4 |
| CPA-6-2 | 2.22E6 | 1.71E6 | 0.51E6 | 22 |  |  |  |
| CPA-7-1 | 2.53E6 | 1.97E6 | 0.57E6 | 22 | 27 | 7.1 | 27 ± 7.1 |
| CPA-7-2 | 2.33E6 | 1.58E6 | 0.75E6 | 32 |  |  |  |
| CPA-8-1 | 2.64E6 | 1.29E6 | 1.34E6 | 51 | 46 | 7.1 | 46 ± 7.1 |
| CPA-8-2 | 2.51E6 | 1.46E6 | 1.04E6 | 41 |  |  |  |
| CPA-9-1 | 2.29E6 | 1.33E6 | 0.96E6 | 41 | 36.5 | 6.4 | 36.5 ± 6.4 |
| CPA-9-2 | 2.34E6 | 1.58E6 | 0.76E6 | 32 |  |  |  |
| CPA-10-1 | 2.37E6 | 2.24E6 | 0.13E6 | 5 | 3.5 | 2.1 | 3.5 ± 2.1 |
| CPA-10-2 | 2.21E6 | 2.26E6 | 0.05E6 | 2 |  |  |  |
| CPA-11-1 | 2.92E6 | 1.53E6 | 1.39E6 | 47 | 41 | 8.5 | 41 ± 8.5 |
| CPA-11-2 | 2.48E6 | 1.61E6 | 0.87E6 | 35 |  |  |  |
| CPA-12-1 | 2.33E6 | 1.25E6 | 1.07E6 | 46 | 50.5 | 6.4 | 50.5 ± 6.4 |
| CPA-12-2 | 2.50E6 | 1.12E6 | 1.38E6 | 55 |  |  |  |
| CPA-13-1 | 2.50E6 | 1.80E6 | 0.70E6 | 28 | 28.5 | 0.7 | 28.5 ± 0.7 |
| CPA-13-2 | 2.37E6 | 1.66E6 | 0.70E6 | 29 |  |  |  |
| CPA-14-1 | 2.50E6 | 1.16E6 | 1.34E6 | 53 | 50.5 | 3.5 | 50.5 ± 3.5 |
| CPA-14-2 | 2.29E6 | 1.18E6 | 1.11E6 | 48 |  |  |  |
| CPA-15-1 | 2.29E6 | 1.18E6 | 1.11E6 | 48 | 39 | 12.7 | 39 ± 12.7 |
| CPA-15-2 | 2.75E6 | 1.90E6 | 0.84E6 | 30 |  |  |  |
| CPA-16-1 | 2.95E6 | 1.10E6 | 1.85E6 | 62 | 61 | 1.4 | 61 ± 1.4 |
| CPA-16-2 | 2.88E6 | 1.13E6 | 1.74E6 | 60 |  |  |  |
| CPA-17-1 | 2.66E6 | 2.67E6 | 0.01E6 | 0 | 1.5 | 2.1 | 1.5 ± 2.1 |
| CPA-17-2 | 2.52E6 | 2.62E6 | 0.10E6 | 3 |  |  |  |
| CPA-18-1 | 3.00E6 | 0.91E6 | 2.09E6 | 69 | 36.5 | 46.0 | 36.5 ± 46.0 |
| CPA-18-2 | 2.43E6 | 2.31E6 | 0.12E6 | 4 |  |  |  |
| CPA-19-1 | 2.17E6 | 1.66E6 | 0.51E6 | 23 | 26 | 4.2 | 26 ± 4.2 |
| CPA-19-2 | 2.23E6 | 1.57E6 | 0.65E6 | 29 |  |  |  |
| CPA-20-1 | 2.29E6 | 1.31E6 | 0.98E6 | 42 | 51 | 12.7 | 51 ± 12.7 |
| CPA-20-2 | 2.31E6 | 0.90E6 | 1.40E6 | 60 |  |  |  |
| CPA-21-1 | 2.25E6 | 1.50E6 | 0.75E6 | 33 | 43.5 | 14.8 | 43.5 ± 14.8 |
| CPA-21-2 | 2.17E6 | 0.99E6 | 1.18E6 | 54 |  |  |  |
| CPA-22-1 | 2.26E6 | 1.05E6 | 1.20E6 | 53 | 59 | 8.5 | 59 ± 8.5 |
| CPA-22-2 | 2.32E6 | 0.80E6 | 1.52E6 | 65 |  |  |  |

TABLE 8-continued

|  | Total cells (×10⁶ cells/mL) | Non-viable cells (×10⁶ cells/mL) | Viable cells (×10⁵ cells/mL) | Cell viability (%) | Avg. | SD | Cell viability (mean ± SD) |
|---|---|---|---|---|---|---|---|
| CPA-23-1 | 2.31E6 | 1.74E6 | 0.57E6 | 24 | 32.5 | 12.0 | 32.5 ± 12.0 |
| CPA-23-2 | 2.26E6 | 1.31E6 | 0.95E6 | 41 | | | |
| CPA-24-1 | 2.45E6 | 1.20E6 | 1.25E6 | 51 | 47.5 | 4.9 | 47.5 ± 4.9 |
| CPA-24-2 | 2.46E6 | 1.36E6 | 1.10E6 | 44 | | | |
| CPA-25-1 | 2.06E6 | 0.56E6 | 1.49E6 | 72 | 66 | 8.5 | 66 ± 8.5 |
| CPA-25-2 | 2.39E6 | 0.93E6 | 1.45E6 | 60 | | | |
| CPA-26-1 | 2.70E6 | 1.67E6 | 1.02E6 | 37 | 42 | 7.1 | 42 ± 7.1 |
| CPA-26-2 | 2.77E6 | 1.46E6 | 1.30E6 | 47 | | | |
| CPA-27-1 | 2.33E6 | 2.09E6 | 0.23E6 | 9 | 14.5 | 7.8 | 14.5 ± 7.8 |
| CPA-27-2 | 2.35E6 | 2.94E6 | 0.59E6 | 20 | | | |

CPA-1 to CPA-27 are different samples. The control samples are DMSO-1, DMSO-2, Complete-1 and Complete-2.

DISCUSSION

The results show that the post-thaw viability of the cells cryopreserved using an embodiment of the present cryopreservation composition (Complete-CPA, Complete-1, and Complete-2) was above 80%, which was comparable to that of the cryopreservation composition containing DMSO (DMSO-CPA, DMSO-1, and DMSO-2).

The results further show that removing any of the three components (macromolecules, sugars and permeating cryoprotectants) from the cryopreservation composition, or using the component at a non-optimal concentration, would decrease the post-thaw cell viability.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description is offered by way of illustration only and not as a limitation.

What is claimed is:

1. A cryopreservation composition comprising:
    (1) about 2% (w/v) to about 20% (w/v) of polyethylene glycol;
    (2) about 0.1 M to about 0.5 M of a saccharide; and
    (3) about 1% (w/v) to about 10% (w/v) of gelatin,
    wherein the unit of % (w/v) and the unit of M are based on the total volume of the cryopreservation composition.

2. The cryopreservation composition of claim 1, wherein the saccharide comprises sucrose, trehalose, or a combination thereof.

3. The cryopreservation composition of claim 1, wherein the gelatin has a molecular weight ranging from about 50 kDa to about 200 kDa.

4. The cryopreservation composition of claim 1, substantially free of DMSO.

5. The cryopreservation composition of claim 1, further comprising an amino acid, a cytokine, a lipid, a growth factor, an antibiotic, an antimycotic, a steroid hormone, a protein hormone, or a combination thereof.

6. The cryopreservation composition of claim 1, further comprising one or more cells.

7. The cryopreservation composition of claim 6, in a cryopreserved state.

8. The cryopreservation composition of claim 6, wherein the cells are present at a concentration ranging from about $10^5$ cells/ml to about $10^7$ cells/ml.

9. The cryopreservation composition of claim 1, comprising:
    about 1% (w/v) to about 5% (w/v) of gelatin.

10. The cryopreservation composition of claim 9, further comprising one or more cells.

11. The cryopreservation composition of claim 10, in a cryopreserved state.

12. The cryopreservation composition of claim 9, wherein the cells are present at a concentration ranging from about $10^5$ cells/ml to about $10^7$ cells/ml.

13. The cryopreservation composition of claim 1, wherein the saccharide comprises sucrose, sorbitol, glucose, fructose, galactose, trehalose, mannose, maltose, or combinations thereof.

14. The cryopreservation composition of claim 9, wherein the saccharide comprises sucrose, sorbitol, glucose, fructose, galactose, trehalose, mannose, maltose, or combinations thereof.

15. A kit comprising the cryopreservation composition of claim 1.

16. A method for cryopreserving one or more cells, the method comprising the steps of:
    (a) mixing the one or more cells with the cryopreservation composition of claim 1 to form a mixture, and
    (b) freezing the mixture.

17. The method of claim 16, wherein the cells are mammalian cells.

18. The method of claim 16, wherein the cells are human, porcine, canine, equine or bovine cells.

19. The method of claim 16, wherein the cells comprise tumor cells.

20. The method of claim 16, wherein the cells comprise fibroblasts.

21. The method of claim 16, wherein the cells comprise stem cells.

22. The method of claim 16, wherein the mixture is frozen at a temperature ranging from about −70° C. to about −200° C.

23. The method of claim 16, wherein the cells are present in the mixture at a concentration ranging from about $10^5$ cells/ml to about $10^7$ cells/ml.

24. The method of claim 16, wherein the cryopreservation composition is substantially free of DMSO.

25. The method of claim 16, further comprising the step (c) thawing the frozen mixture.

26. The method of claim 25, wherein the cells have a post-thaw viability of at least 70%.

27. The method of claim 25, wherein the cells have a post-thaw viability of at least 80%.

* * * * *